(12) United States Patent
Ayiyama et al.

(10) Patent No.: US 8,096,977 B2
(45) Date of Patent: Jan. 17, 2012

(54) PROTECTOR AND NEEDLE SET

(75) Inventors: Masahiro Ayiyama, Fujinomiya (JP);
Masahide Murakoshi,
Ashigarakami-gun (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 485 days.

(21) Appl. No.: 12/084,152

(22) PCT Filed: Oct. 24, 2006

(86) PCT No.: PCT/JP2006/321111
§ 371 (c)(1),
(2), (4) Date: Apr. 25, 2008

(87) PCT Pub. No.: WO2007/049585
PCT Pub. Date: May 3, 2007

(65) Prior Publication Data
US 2009/0099528 A1    Apr. 16, 2009

(30) Foreign Application Priority Data
Oct. 28, 2005 (JP) .................. 2005-314149

(51) Int. Cl.
*A61M 5/00* (2006.01)
*A61M 5/32* (2006.01)
*A61M 5/178* (2006.01)
*A61B 5/00* (2006.01)
*B65D 81/00* (2006.01)

(52) U.S. Cl. ........ 604/171; 128/919; 600/573; 600/576; 604/162; 604/163; 604/164.07; 604/164.08; 604/192; 604/198; 604/263

(58) Field of Classification Search .................. 128/919; 604/164.01, 164.07, 164.08, 164.09, 164.11, 604/165.01, 165.02, 165.04, 167.01, 171, 604/263, 264, 93.01, 110, 272, 48, 6.16; 600/573, 576, 582
See application file for complete search history.

(56) References Cited

U.S. PATENT DOCUMENTS
4,682,981 A * 7/1987 Suzuki et al. .................. 604/158
(Continued)

FOREIGN PATENT DOCUMENTS
JP    2 237 201 A    5/1991
(Continued)

OTHER PUBLICATIONS
PCT/ISA/210—International Search Report.
(Continued)

*Primary Examiner* — Kevin C Sirmons
*Assistant Examiner* — Shefali Patel
(74) *Attorney, Agent, or Firm* — Buchanan Ingersoll & Rooney PC

(57) ABSTRACT

A protector comprising an inner tube, a lid connected to an upper opening of the inner tube through a hinge, and an outer tube for holding the inner tube in an inner cavity part of the outer tube. A blood collecting needle to which a tube is connected is stored in the inner tube. The inner tube comprises an annular seat face which seats on the base end part of a hub formed integrally with the blood collecting needle when the blood collecting needle moves downward. An operation lever extending downward is installed at the side of the lid, and an end part of the operation lever is slightly projected outward. When the blood collecting needle is moved, the inner tube is pulled integrally with the tube by the annular seat face to be slid relative to the outer tube until the end part abuts on the lower end part of an operation hole. Then, the lid is closed and the blood collecting needle is stored in the inner tube.

11 Claims, 27 Drawing Sheets

U.S. PATENT DOCUMENTS

| | | | |
|---|---|---|---|
| 4,791,937 A * | 12/1988 | Wang | 600/565 |
| 4,846,811 A * | 7/1989 | Vanderhoof | 604/263 |
| 4,926,877 A * | 5/1990 | Bookwalter | 600/567 |
| 4,995,869 A * | 2/1991 | McCarthy | 604/110 |
| 5,040,691 A * | 8/1991 | Hayes et al. | 215/216 |
| 5,197,956 A * | 3/1993 | Brizuela | 604/171 |
| 5,401,250 A * | 3/1995 | Shields | 604/192 |
| 5,480,389 A * | 1/1996 | McWha et al. | 604/165.02 |
| 5,540,662 A * | 7/1996 | Nicholson | 604/110 |
| 5,827,305 A * | 10/1998 | Gordon | 606/159 |
| 5,941,850 A * | 8/1999 | Shah et al. | 604/110 |
| 6,077,248 A * | 6/2000 | Zumschlinge | 604/167.01 |
| 6,165,157 A | 12/2000 | Dillon et al. | |
| 6,193,694 B1 * | 2/2001 | Bell et al. | 604/192 |
| 6,626,868 B1 * | 9/2003 | Prestidge et al. | 604/158 |
| 6,632,201 B1 * | 10/2003 | Mathias et al. | 604/263 |
| 6,666,847 B2 * | 12/2003 | Secrest et al. | 604/164.01 |
| 6,712,790 B1 * | 3/2004 | Prestidge et al. | 604/164.06 |
| 6,770,053 B2 * | 8/2004 | Scarfone et al. | 604/117 |
| 6,827,692 B2 * | 12/2004 | Castellacci | 600/567 |
| 2003/0060774 A1 * | 3/2003 | Woehr et al. | 604/192 |
| 2004/0078003 A1 * | 4/2004 | Smith et al. | 604/164.08 |
| 2004/0116855 A1 * | 6/2004 | Popov et al. | 604/110 |

FOREIGN PATENT DOCUMENTS

| | | |
|---|---|---|
| JP | 9-511935 A | 2/1997 |
| JP | 2 345 854 A | 7/2000 |
| JP | 2000-342686 A | 12/2000 |
| JP | 2003-320029 A | 11/2003 |
| JP | 3578459 B2 | 7/2004 |

OTHER PUBLICATIONS

PCT/ISA/237—Written Opiion.

* cited by examiner

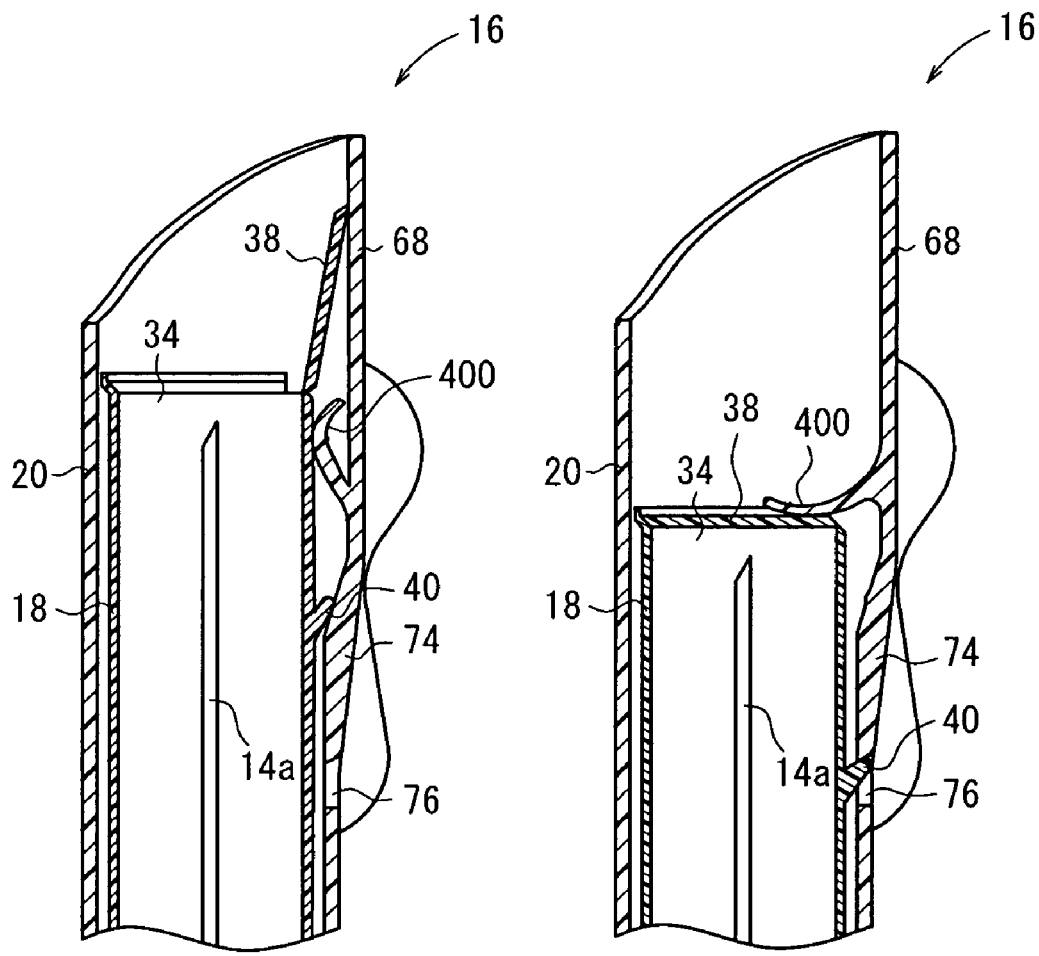

PROTECTOR AND NEEDLE SET

CROSS REFERENCE TO RELATED APPLICATIONS

Applicant claims priority under 35 U.S.C. §119 of Japanese Application No. 2005-314149 filed Oct. 28, 2005. Applicant also claims priority under 35 USC §365 of PCT/JP2006/321111 filed Oct. 24, 2006. The international application under PCT article 21(2) was not published in English.

TECHNICAL FIELD

This invention relates to a protector for protecting a needle for medical treatment used for blood collection, blood transfusion, infusion and so forth and a needle set including a needle and a protector.

BACKGROUND ART

A needle for medical treatment is known, which is connected to and used with a blood collection bag, an infusion bag or the like in blood collection, blood transfusion, infusion and so forth is known. Preferably, a needle after being used is covered with a protector such as that disclosed in Japanese Laid-Open Patent Publication No. 2000-342686 or Japanese Patent No. 3578459 so that it may not be touched inadvertently. According to such a protector, the needle is suitably accommodated into the protector by a very simple operation of pulling a tube after the needle is used.

Incidentally, in the protector disclosed in Japanese Laid-Open Patent Publication No. 2000-342686 and Japanese Patent No. 3578459, although side surfaces of the needle can be covered, the tip of the protector remains open, and there is the possibility that blood sticking to the outer surface of the needle and blood remaining in the inside of the needle may leak out from the tip of the protector.

Further, since it is difficult to confirm that the needle is accommodated up to the tip thereof in the protector certainly, there is a possibility that the needle point may be touched.

DISCLOSURE OF THE INVENTION

It is an object of the present invention to provide a protector which can certainly cover a needle after being used to prevent the needle point from being touched and prevent blood from leaking out from the tip of the protector, and a needle set which includes a needle and the protector.

It is another object of the present invention to provide a protector which certainly covers a needle after being used to prevent the needle point from being touched and prevent blood from leaking out from the rear end of the protector, and a needle set which includes a needle and the protector.

According to the present invention, there is provided a protector into which a tube having a needle provided at one end thereof is inserted and which accommodates the needle, having an inner tube including a stopper which is brought into contact with the needle when the needle is accommodated in the inner tube from one opening thereof, and a lid connected to the one opening through a hinge, an outer tube configured to hold the inner tube for sliding movement in a cavity portion thereof, and an operation lever provided on an outer surface of the lid or an inner surface of the outer tube, the operation lever being configured to operate, when the needle accommodated in the inner tube is brought into contact with the stopper to slidably move the inner tube with respect to the outer tube, so as to close the lid.

Further, according to the present invention, there is provided a needle set including the protector described above, and a needle to which the tube is connected.

With such a protector and a needle set as described above, since the inner tube is slidably moved with respect to the outer tube and the lid is closed by the operation lever in an interlocking relationship with movement of the needle and the tube, the needle accommodated in the inner tube is covered certainly, and leakage of blood from the tip of the protector can be prevented.

In this instance, if the protector further includes holding means configured to hold the lid in an open state before the lid is closed, then when the needle is used, the lid is open stably and does not make an obstacle to movement of the needle or the tube.

The protector may be configured such that the operation lever is provided on the outer surface of the lid and the protector further includes operation means configured to operate the operation lever so as to be brought into contact with the outer tube to close the lid, when the inner tube slidably moves with respect to the outer tube, so that the operation lever may be operated certainly.

The protector may be configured such that the operation lever is provided on the inner surface of the outer tube and the operation lever is configured to be brought into contact with the lid to close the lid, when the inner tube slidably moves with respect to the outer tube.

The protector may further include locking means configured to prevent reverse movement of the inner tube, when the inner tube slidably moves by a predetermined amount with respect to the outer tube.

When the protector further includes positioning means configured to prevent the inner tube from rotating with respect to the outer tube, the operation lever is not displaced and the lid is closed certainly.

When the operation lever is configured to bias the lid in the closing direction after the lid is closed, the lid can be closed more certainly.

Further, when the protector is configured such that the inner tube has a plurality of pawls provided at an end portion of another opening and the outer tube has a tapering portion provided on an inner surface thereof and besides the pawls are brought into contact with the tapering portion and displaced to the inner side, when the inner tube slidably moves with respect to the outer tube, the plural pawls can be in close contact with the outer surface of the tube to prevent blood from leaking out from the rear end of the protector, by a simple and convenient operation of moving the needle. Further, when the number of the pawls is two, the tube can be closed up.

BRIEF DESCRIPTION OF THE DRAWINGS

FIG. 27A is a sectional side elevational view of a modification to the protector according to the present invention in an initial state; and FIG. 27B is a sectional side elevational view showing the modification to the protector according to the first embodiment in a state in which a lid is closed;

BEST MODE FOR CARRYING OUT THE INVENTION

Figure 1:
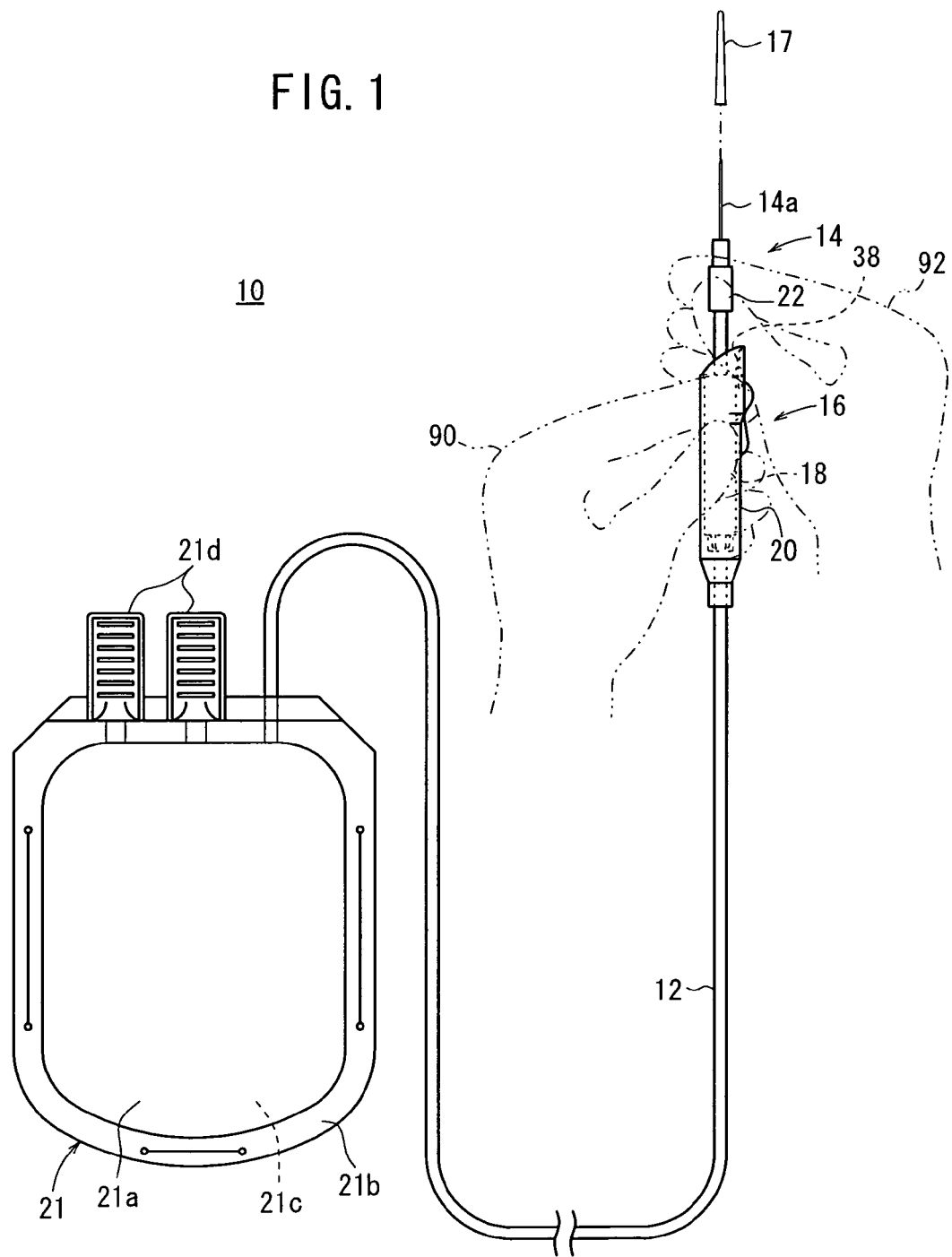
FIG. 1 is a view showing a configuration of a needle set according to a first embodiment.

In the following, a protector and a needle set according to the present invention are described in connection with first to fourth embodiments with reference to FIGS. 1 to 27B of the accompanying drawings. It is to be noted that, although the upward and downward directions and lengthwise and breadthwise directions are specified in accordance with those in the drawings for the convenience of description, when the protector and the needle set are actually used, the directions of them are not restricted to them.

As shown in FIG. 1, a needle set 10 according to the first embodiment includes a blood collection needle 14 to which a tube 12 is connected, a protector 16 for accommodating and protecting the blood collection needle 14 after being used therein, and a cap 17 for protecting the cap 17 before being used. The protector 16 includes an inner tube 18, and an outer tube 20 holding the inner tube 18 for sliding movement in a cavity portion thereof.

As the material for the inner tube 18, polyolefin or the like can be used. Meanwhile, as the material of the outer tube 20, polyolefin or the like can be used. Further, for the tube 12, soft polyvinyl chloride, polyolefin elastomer (for example, polyethylene elastomer, polypropylene elastomer) or the like can be used.

The tube 12 has another end connected to a blood collection bag 21 (blood bag). The blood collection bag 21 is formed such that flexible sheet members 21a made of a soft resin material such as polyvinyl chloride are placed one on the other and welded (thermally welded, high frequency welded) or bonded at sealing portions 21b on circumferential edges thereof so as to have a form of a bag. A storage space 21c for storing collected blood is formed as an inside space surrounded by the sealing portions 21b of the blood collection bag 21. Further, two opening portions 21d openably sealed with peel tabs are formed at an upper portion of the blood collection bag 21. It is to be noted that anticoagulant such as solution of heparin sodium, ACD-A solution, CPD solution or CPDA-1 solution may be accommodated in advance in the storage space 21c. It is to be noted that the connection destination of the tube 12 is not limited to the blood collection bag 21 as a single item but may be a multiple type blood bag or the like. A branch tube for collecting the blood for inspection may be connected to an intermediate portion of the tube 12.

Figure 2:
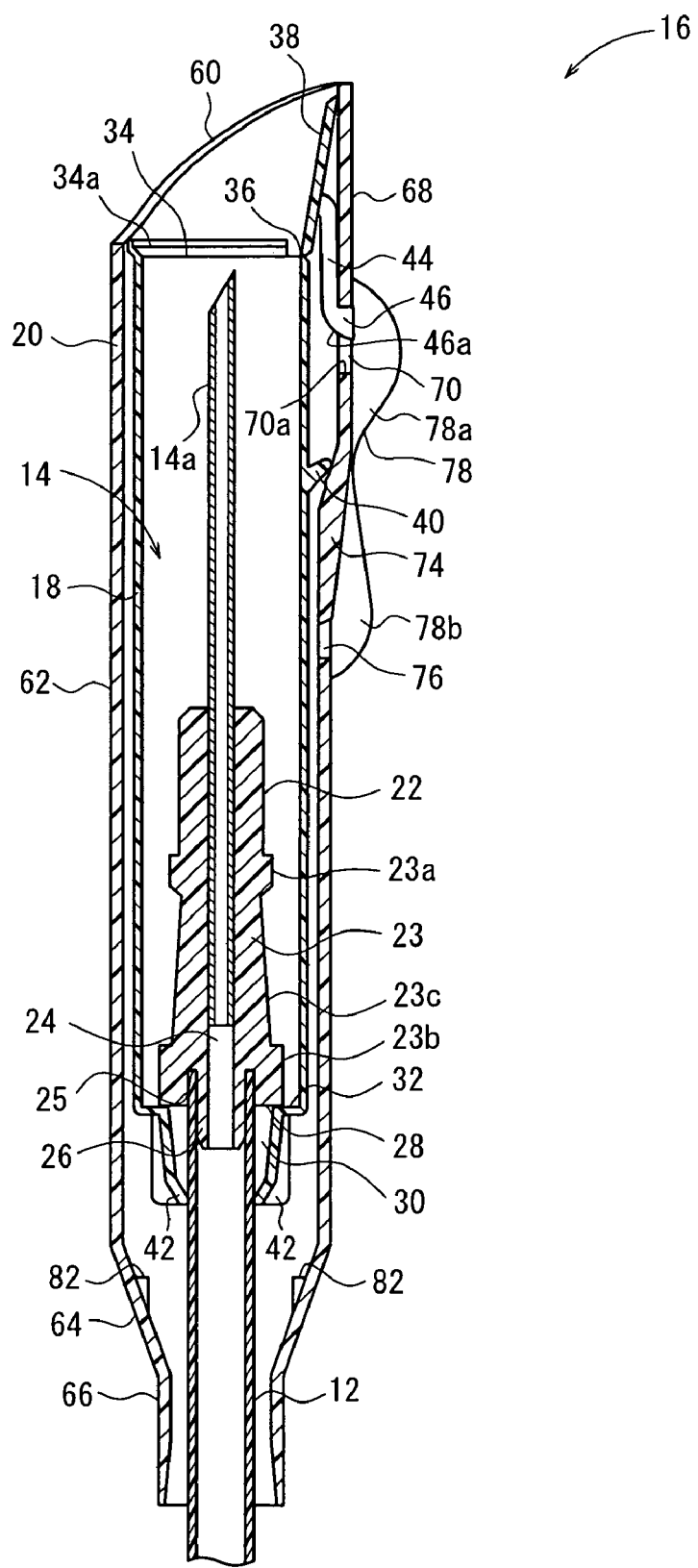
FIG. 2 is a sectional side elevational view of a protector according to the first embodiment.
Figure 3:
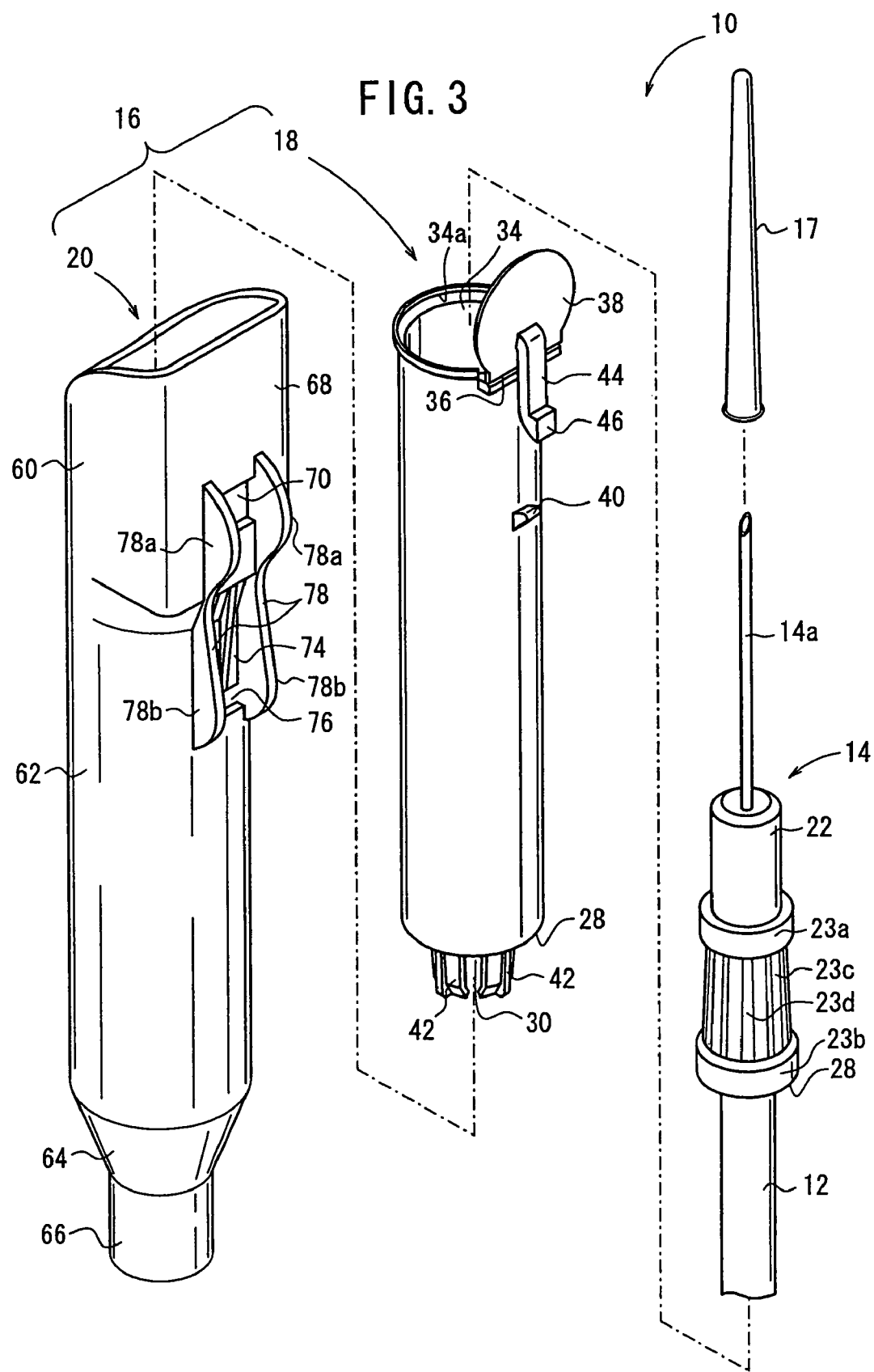
FIG. 3 is an exploded perspective view of the protector according to the first embodiment.

As shown in FIGS. 2 and 3, the blood collection needle 14 includes a needle body 14a and a hub 22. The needle body 14a is a hollow needle and made of a metal such as stainless steel, aluminum or titanium or a hard resin material such as polyphenylene sulfide. The hub 22 has a hub body 23, a passage 24 for holding the needle body 14a at the center thereof, and an annular concave portion 25 and a protrusion 26 provided on the base end side thereof such that the tube 12 is connected thereto. The needle body 14a is secured (or connected) liquid-tight in a state in which it is fitted in the passage 24, while the end portion of the tube 12 is fitted in the annular concave-portion 25 and secured liquid-tight. A base end portion 28 of the hub body 23 is formed with a diameter greater than that of the tube 12.

The hub body 23 has a first flange 23a provided at a substantially central portion of a side surface thereof in the longitudinal direction and a second flange 23b provided at a lower end portion of the side surface thereof, and a portion thereof defined by the first flange 23a and the second flange 23b becomes a relatively depressed annular concave portion 23c. A large number of vertical ribs 23d are provided in the annular concave portion 23c. The vertical ribs 23d act as non-slip elements when the hub 22 is to be gripped.

The inner tube 18 has a hollow shape in which the tube 12 and the blood collection needle 14 are fitted. The inner tube 18 has an annular seat surface (stopper) 32 for seating the base end portion 28 of the hub 22 when the tube 12 is pulled from a lower opening (one opening) 30, a hinge 36 provided at an upper opening (the other opening) 34 of the inner tube 18, a lid 38 connected to the inner tube 18 through the hinge 36, a protrusion 40 provided on the outer surface of the inner tube 18, and four pawls 42 extending downwardly from an end portion of the lower opening 30. The annular seat surface 32, hinge 36, lid 38, protrusion 40 and pawls 42 are molded integrally with the body portion of the inner tube 18.

The annular seat surface 32 is a step provided at a lower portion of the inner surface of the inner tube 18 and is set so as to have a diameter greater than that of the tube 12 but smaller than that of the base end portion 28. The distance from the upper opening 34 to the annular seat surface 32 is set a little longer than the blood collection needle 14 including the hub 22.

The hinge 36 is a thin resin member and connects an upper end portion of the inner tube 18 and the lid 38. Further, the hinge 36 has resiliently biases, in an initial state thereof, the lid 38 slightly in an outward direction. The initial state is a state before the tube 12 is pulled and is a state in which the inner tube 18 does not start sliding movement thereof with respect to the outer tube 20 as seen in FIG. 2.

The lid 38 is a circular resin plate which can close up the upper opening 34 of the inner tube 18 and is set, in an initial state thereof, to a direction substantially perpendicular to the upper opening 34. An operation lever 44 is provided on an outer surface of the lid 38 and extends downwardly. An end portion 46 of the operation lever 44 has a form of a projection protruding a little in an outward direction, and an inner side surface 46a of the end portion 46 is formed as an inclined surface. The upper opening 34 is formed with a rather great thickness on the outer side of an edge portion thereof such that the lid 38 may be fitted therein, and has a shallow annular groove 34a provided on the inner side thereof.

The protrusion 40 is set to a position a little lower than the upper opening 34 and has a wedge shape having a triangular shape as viewed in side elevation and protruding a little in an obliquely upward direction.

Figure 4:
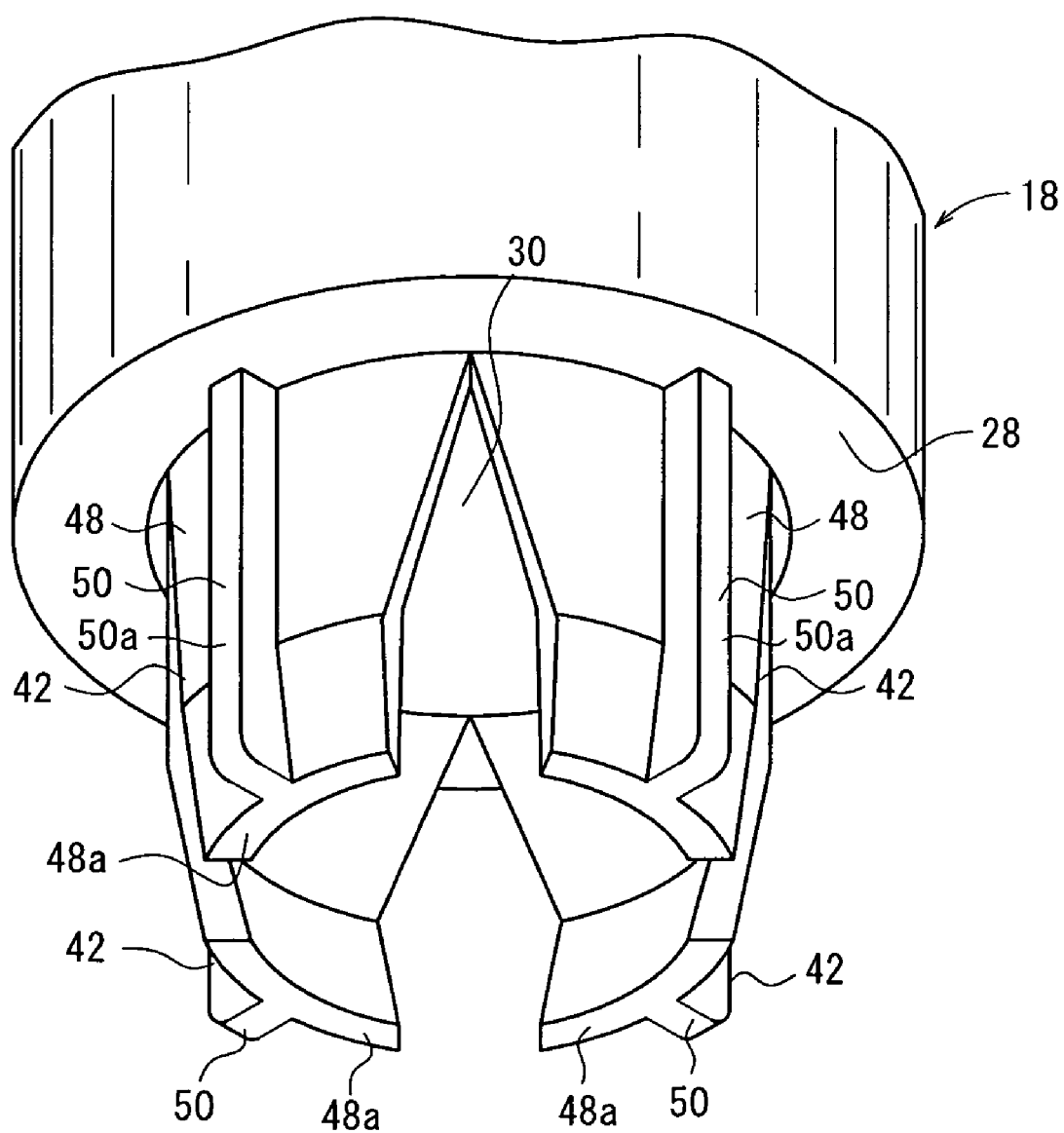
FIG. 4 is a perspective view of pawls provided at a lower opening of an inner tube.
Figure 5:
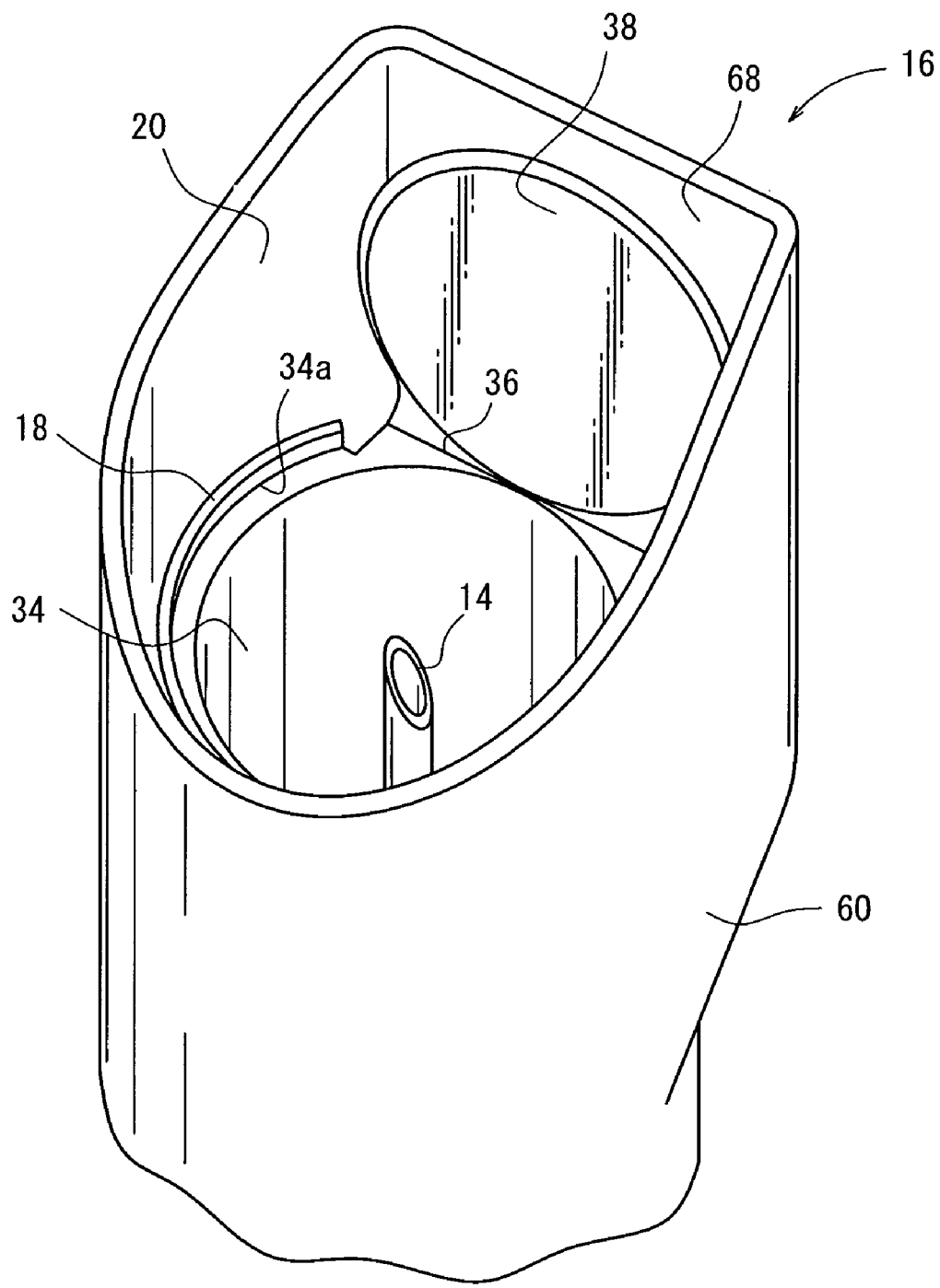
FIG. 5 is an enlarged perspective view of an upper portion of the protector according to the first embodiment.

As shown in FIG. 4, the four pawls 42 are provided in an equally spaced relationship from each other at an end portion of the lower opening 30. Each of the pawls 42 has a plate portion 48 having an arcuate cross section and inclined a little to the inner side in a downward direction, and a guide rib 50 provided on the outer surface side of the plate portion 48. A tip portion 48a of the plate portion 48 is formed such that it is inclined with a steeper inclination to the inner side and has a width decreasing to the tip side. The guide rib 50 is a projection extending in a vertical direction at a middle portion of the outer surface side of each plate portion 48, and an outer side surface 50a is set in such a manner as to have a plane parallel to the axis of the inner tube 18. The outer side surface 50a is chamfered arcuately at a lower end portion thereof.

The outer tube 20 has an upper open tube 60, a tube body 62 of a middle height portion, a tapering portion 64 and a lower open tube 66 provided in the order from above thereon. The upper open tube 60 has a substantially horseshoe shape which is a combination of a semi-circular shape and a square shape as viewed in plan, and the diameter of the semi-circular portion is equal to the diameter of the tube body 62 (refer to FIG. 5). A back surface plate 68 opposing to the semi-circular portion is set to an area of a degree such that the lid 38 rests against the back surface plate 68, and a lower end portion of the back surface plate 68 is connected smoothly to the tube body 62. The upper open tube 60 has an arcuate shape as viewed in side elevation, and the central point of the arcuate portion substantially coincides with the position of the hinge 36 of the inner tube 18.

The tube body 62 is elongated in the vertical direction when compared with the other portions, and is formed with a diameter a little greater than that of the inner tube 18. The tapering portion 64 connects the tube body 62 and the lower open tube 66 to each other and has a diameter which decreases downwardly. The lower open tube 66 is a tube having a diameter a little greater and having a length smaller than those of the tube 12, and prevents the tube 12 from being shaken or bent inadvertently with respect to the protector 16.

Figure 6:
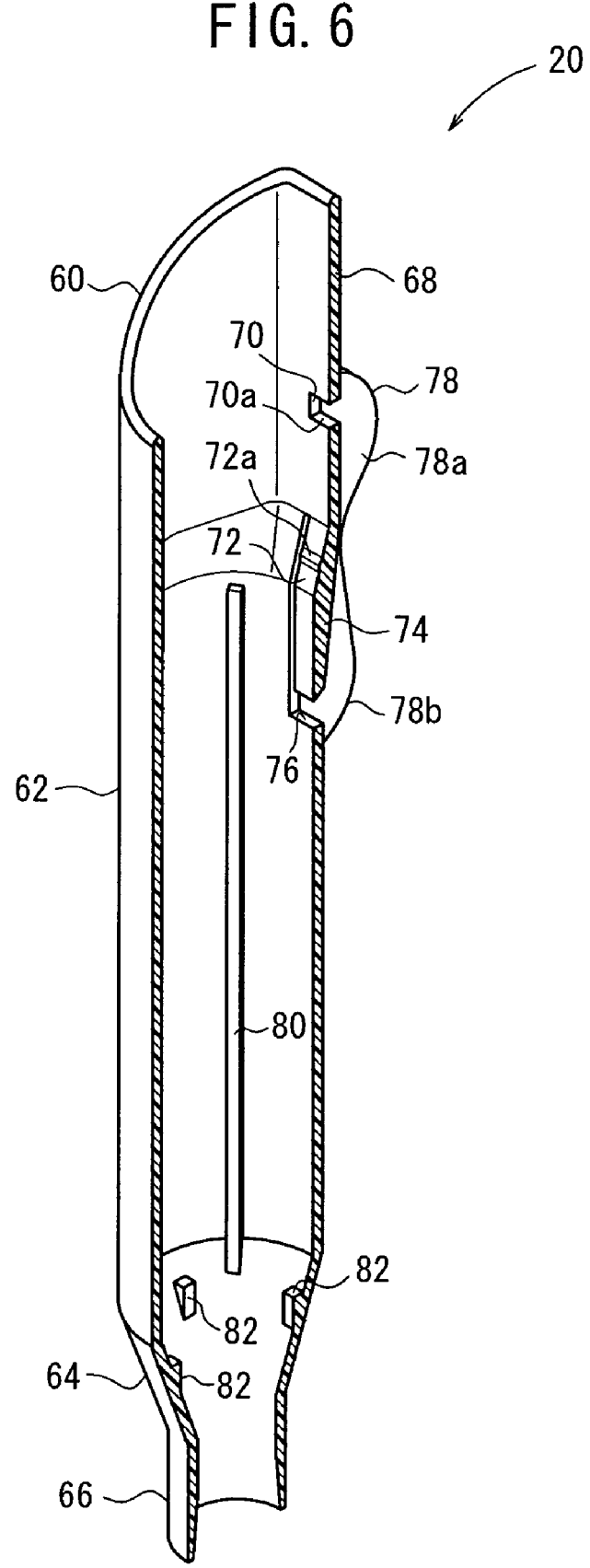
FIG. 6 is a partial sectional perspective view of an outer tube.

Further, as shown in FIG. 6, the outer tube 20 has an operation hole (operation means) 70, a guide groove 72, an inner tube locking pawl 74, and an engaging hole 76. The operation hole 70 is a portion for contacting the operation lever 44 when the inner tube 18 slidably moves, and is a small quadrangular hole provided at a location a little lower than the center of the back surface plate 68. The guide groove 72 is a shallow groove for guiding the protrusion 40 when the inner tube 18 slidably moves, and is provided from a lower end portion of the back surface plate 68 to an upper portion of the tube body 62. The guide groove 72 is set to a width substantially equal to that of the protrusion 40. Since the connecting portion between the back surface plate 68 and the tube body 62 is inclined moderately, an upper portion of the guide groove 72 is inclined along the connecting portion. Further, a low triangular protrusion 72a is provided at a substantially middle height portion of the inclined portion.

The engaging hole 76 is a quadrangular hole provided in a lower end portion of the guide groove 72. The inner tube locking pawl 74 is an elastic piece which forms a bottom portion of the guide groove 72 of the tube body 62, and is connected at an upper end portion thereof to and extends downwardly from the tube body 62. The inner tube locking pawl 74 acts such that, when the inner tube 18 slidably moves, the inner tube locking pawl 74 is elastically pushed outwardly by the protrusion 40 and returns, when the protrusion 40 reaches the engaging hole 76, to the original position thereby to prevent reverse movement of the inner tube 18. Accordingly, locking means is formed by the engaging hole 76 or by the engaging hole 76 and the inner tube locking pawl 74.

The outer tube 20 further has two guards 78 (refer to FIG. 3) provided in the vertical direction at the opposite side portions of the engaging hole 76 from the operation hole 70. Each of the two guards 78 individually has a first swollen portion 78a in the proximity of the operation hole 70 and a second swollen portion 78b in the proximity of the engaging hole 76, and forms two mountain shapes as viewed in side elevation. The first swollen portions 78a are formed in such a manner as to guard the operation lever 44 which projects outwardly from the back surface plate 68. The second swollen portions 78b are formed such that the second swollen portions 78b guard the inner tube locking pawl 74 which is resiliently deformed and projects outwardly.

The outer tube 20 further has four adjustment ribs 80 extending in the axial direction on the inner side surface of the tube body 62, and four abutment stops 82 provided at a substantially middle height on the inner side surface of the tapering portion 64.

Figure 7:
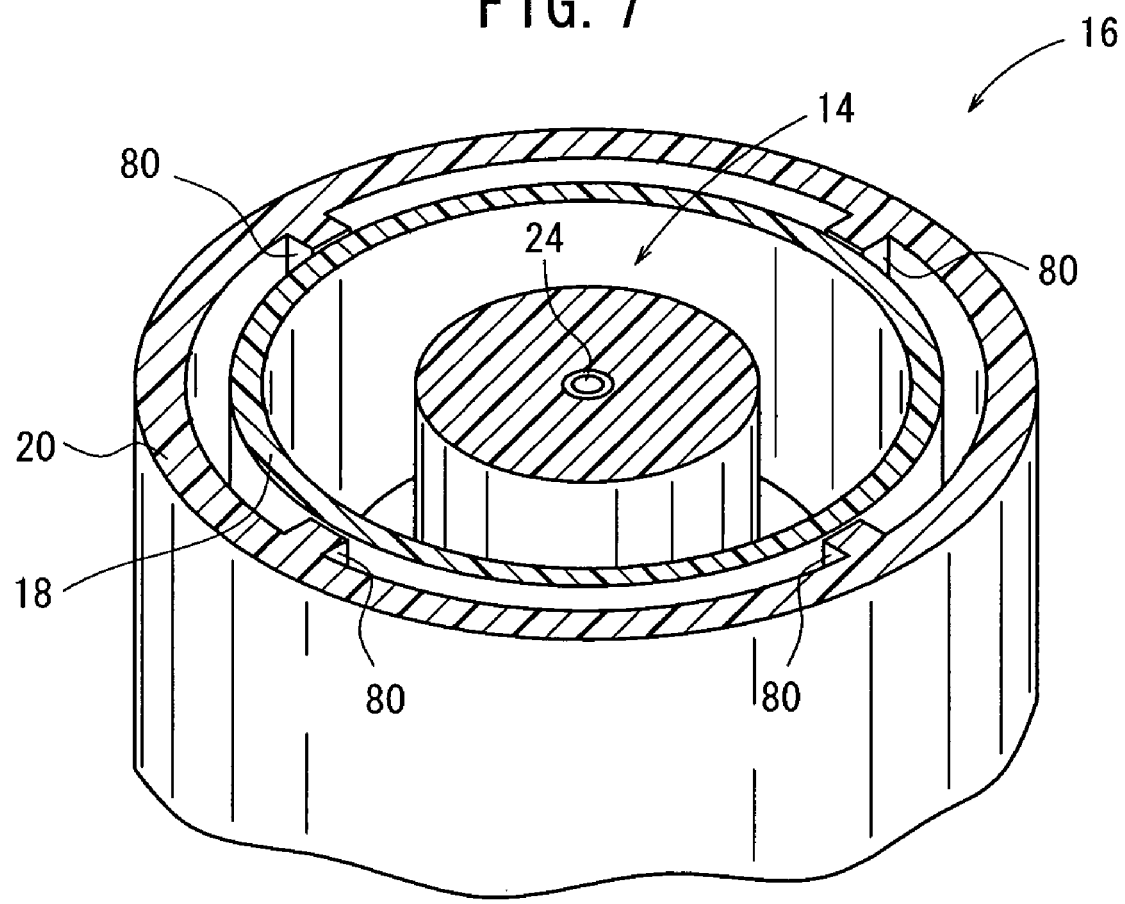
FIG. 7 is a sectional side elevational view of the protector.

As shown in FIG. 7, the four adjustment ribs 80 are low ribs for holding the inner tube 18 and are equally spaced from each other. The adjustment ribs 80 hold the inner tube 18 in a well-balanced state at four locations and reduce the frictional resistance to the inner tube 18 to permit smooth sliding movement. The four abutment stops 82 are brought into contact with the lower opening 30 to limit the sliding movement to an appropriate amount, when the inner tube 18 slidably moves.

When the inner tube 18 is to be assembled to the outer tube 20 to obtain the protector 16, the inner tube 18 is inserted from the lower opening 30 side thereof into the upper open tube 60 until the protrusion 40 is engaged with an upper end portion of the guide groove 72. Consequently, the lid 38 is brought into slight contact with the back surface plate 68 by an elastic action of the hinge 36, and the open state of the lid 38 with respect to the upper opening 34 is kept stably.

Since the upper end portion of the guide groove 72 is inclined moderately toward the inner side and besides the triangular protrusion 72a is provided at an intermediate portion of the guide groove 72, when the protrusion 40 engages with the triangular protrusion 72a, the inner tube 18 is not inadvertently displaced downwardly but is kept at an initial state thereof which is an appropriate position. Further, since the protrusion 40 has a wedge shape, the inner tube 18 is not removed upwardly, and, even if the protector 16 is directed downwardly, the inner tube 18 does not drop. Furthermore, since the guide groove 72 is set to a width substantially equal to that of the protrusion 40, the inner tube 18 is prevented from rotating with respect to the outer tube 20 and acts as positioning means.

When the protrusion 40 is engaged with the upper end portion of the guide groove 72, the end portion 46 of the operation lever 44 fits into an upper end portion of the operation hole 70. As a result, the end portion 46 acts as positioning means for preventing removal and rotation of the inner tube 18 from and with respect to the outer tube 20 as with the protrusion 40.

Further, lower end portions of the four pawls 42 are disposed at a substantially lower end portion of the tube body 62 and are kept in a non-contacting state with respect to the inner surface of the tube body 62 and the inner surface of the tapering portion 64.

When the protector 16 is to be assembled to the needle set 10, an end portion of the tube 12 is inserted into the outer tube 20 from the upper open tube 60, passed in the inner tube 18, pulled out from the lower open tube 66 and connected to the blood collection bag 21 by a predetermined method (refer to FIG. 1). The protector 16 is disposed at or temporarily secured to a suitable location of the tube 12.

Now, a method of using the needle set 10 and the protector 16 configured in such a manner as described above is described.

An operator such as a person who engages in medical services would remove the cap 17, then grip the hub 22 and puncture the blood collection needle 14 into a blood vessel through the skin of a blood donor (donor) to carry out a predetermined medical process such as blood collection. At this time, the blood introduced from the blood collection needle 14 is stored into the storage space 21c of the blood collection bag 21 through the tube 12.

After a suitable amount of blood is stored into the blood collection bag 21, before the blood collection needle 14 is pulled out from the blood donor, the operator would close up the tube 12 with a clamp or the like and move the protector 16 to a location in the proximity of the hub 22. Thereafter, the operator would grasp the hub 22 by one hand 92 and pull out the blood collection needle 14 from the donor.

Then, the operator would grasp the protector 16 with the other hand 90 as shown in FIG. 1 and release the hub 22 from the one hand 92, and then drop the blood collection needle 14 into the protector 16 and pull the tube 12 downwardly. At this time, since the lid 38 rests against and along the back surface plate 68, it does not make an obstacle to the operation of accommodating the tube 12 and the blood collection needle 14. Further, the lid 38 exhibits an action of guiding the hub 22 into the inner tube 18. Furthermore, since the upper opening 34 of the inner tube 18 is formed with a rather great thickness and the annular groove 34a is provided, the hub 22 or the blood collection needle 14 is less likely to be caught thereby. Since the opening portion of the upper open tube 60 of the outer tube 20 is formed in an obliquely arcuate shape and expanded at the opening thereof, the hub 22 and the needle body 14a can be accommodated readily. The base end portion 28 of the hub 22 accommodated in the inner tube 18 is seated on the annular seat surface 32 as shown in FIG. 2. At this time, the tip of the blood collection needle 14 is disposed a little lower than the upper opening 34 of the inner tube 18. It is to be noted that, when the blood collection needle 14 is accommodated, the direction of the hub 22 with respect to the protector 16 is not limited.

Figure 8:
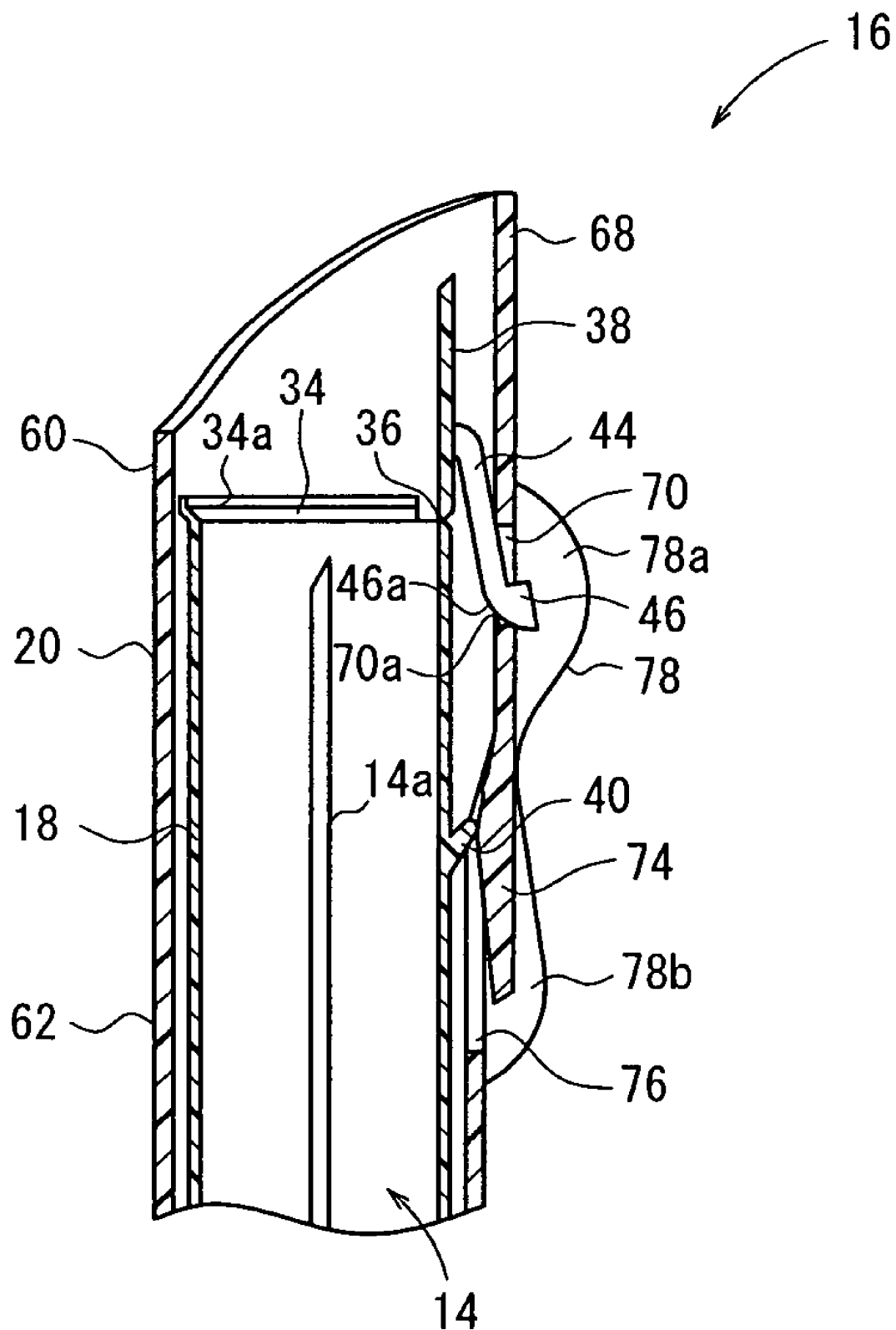
FIG. 8 is a sectional side elevational view showing the protector according to the first embodiment in a state in which the inner tube slidably moves downwardly until a lever is brought into contact with a lower end portion of an operation hole.

Further, by pulling the tube 12 to move the blood collection needle 14, the inner tube 18 moves integrally while the base end portion 28 is engaged with the annular seat surface 32 and slidably moves downwardly with respect to the outer tube 20. By slidably moving the inner tube 18, the protrusion 40 moves along the guide groove 72 as seen in FIG. 8, rides over the triangular protrusion 72a and biases the inner tube locking pawl 74 outwardly. By this, the inner tube locking pawl 74 is resiliently deformed and tilts around an upper end portion thereof such that it is pushed outwardly. Thereupon, since a portion in the proximity of the base end portion of the inner tube locking pawl 74 is pushed by the protrusion 40, it is tilted in a comparatively great amount. Further, the inner side surface 46a of the end portion 46 of the operation lever 44 is brought into contact with a lower end portion 70a of the operation hole 70. Since the inner side surface 46a is an inclined surface, it slidably moves along the lower end portion 70a in such a manner as to be pushed outwardly. In short, the force in the counterclockwise direction in FIG. 8 is applied to the operation lever 44, and based on this, the lid 38 starts tilting motion around the hinge 36 and moves away from the back surface plate 68.

Figure 9:
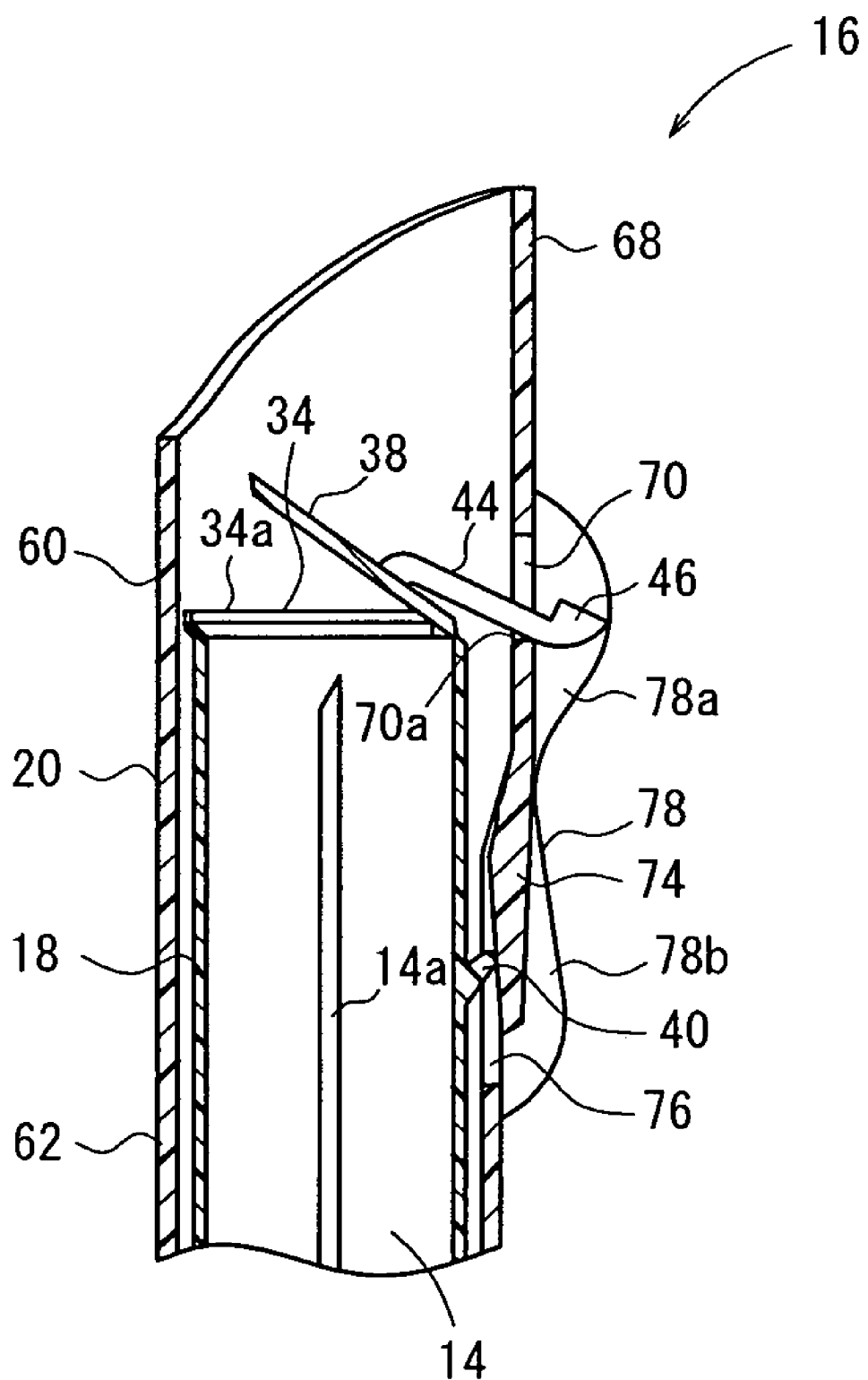
FIG. 9 is a sectional side elevational view showing the protector according to the first embodiment in a state in which the inner tube slidably moves downwardly further and a lid is being closed.

As shown in FIG. 9, as the sliding movement of the inner tube 18 continues, the protrusion 40 further moves downwardly along the guide groove 72, and since the inner tube locking pawl 74 is pushed at a portion in the proximity of the tip portion thereof, the tilting angle decreases. Further, the operation lever 44 is further pushed outwardly by the lower end portion 70a of the operation hole 70, and the lid 38 is further tilted. In this manner, the operation lever 44 is tilted in an interlocking relationship with the sliding movement of the inner tube 18 until the lid 38 closes up the upper opening 34. Further, since the upper open tube 60 has an arcuate shape as viewed in side elevation, when the lid 38 tilts, it does not protrude from the upper open tube 60.

Figure 10:
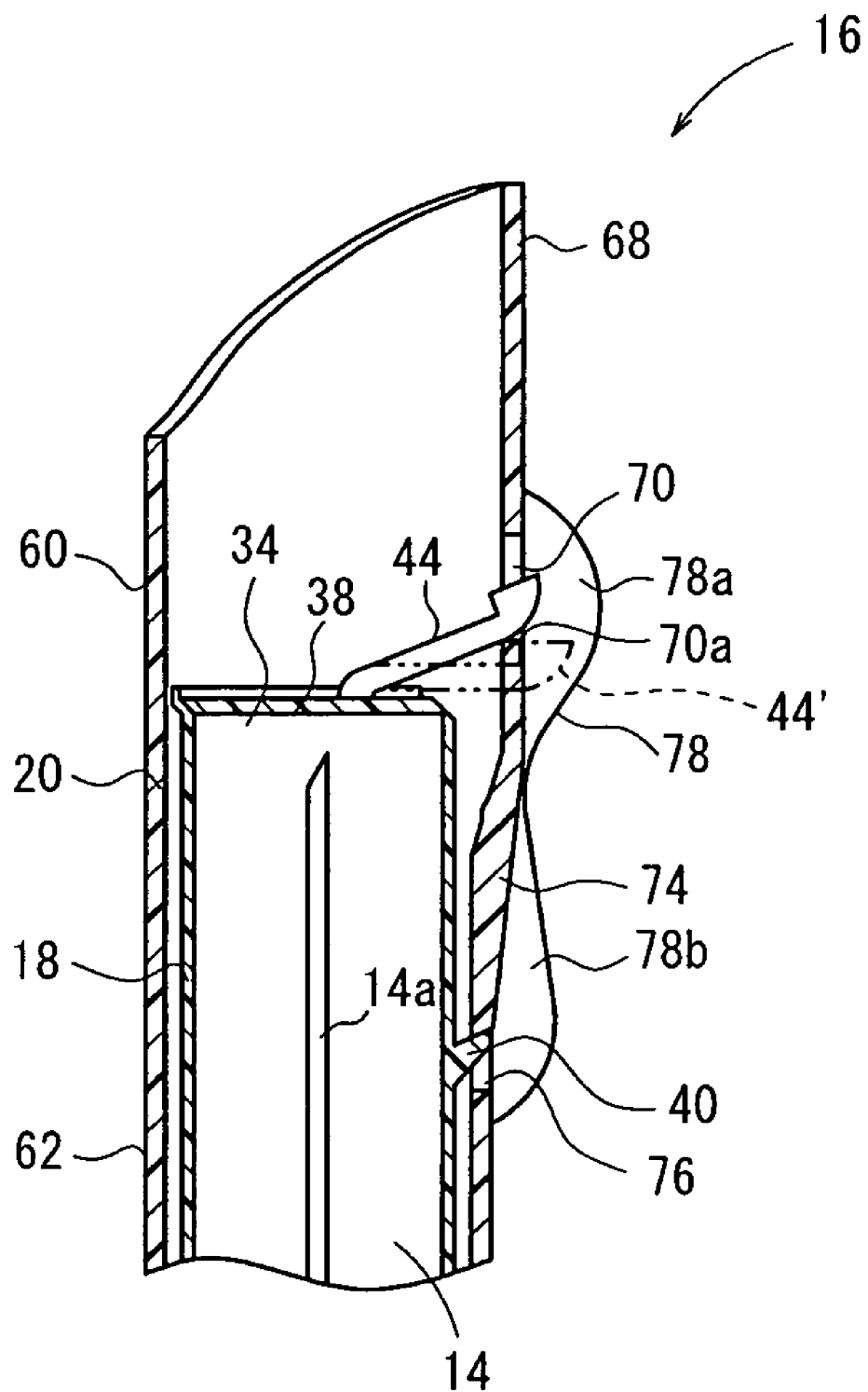
FIG. 10 is a sectional side elevational view showing the protector according to the first embodiment in a state in which the inner tube slidably moves to its operation end position and the lid is closed.

As shown in FIG. 10, as the inner tube 18 is further moved slidably, the protrusion 40 moves along the guide groove 72 and is fitted into the engaging hole 76, and since the inner tube locking pawl 74 is released from the protrusion 40, it returns to its original position rapidly. By the returning of the inner tube locking pawl 74, fine vibration is generated with the protector 16. However, since the lid 38 is closed up already, even if the blood sticking to the blood collection needle 14 should be scattered or the blood should leak out from within the blood collection needle 14, since the blood is intercepted by the inner tube 18 and the lid 38, the blood does not go out to the outside.

Since the protrusion 40 has a wedge shape protruding obliquely upwardly, the protrusion 40 can engage with the lower end portion of the inner tube locking pawl 74 to prevent reverse movement of the inner tube 18. At this time, the inner tube 18 has slidably moved to a position a little lower than that at time at which the lid 38 is closed, and the operation lever 44 is pushed upwardly by the lower end portion 70a of the operation hole 70 and is resiliently deformed farther than its original shape 44' indicated by an alternate long and two short dashes line. Accordingly, the lid 38 is resiliently biased with respect to the upper opening 34 so as to exhibit a sealing action, and can close up the inner tube 18.

Further, since the lower opening 30 is brought into contact with the abutment stops 82 of the outer tube 20, the inner tube 18 slidably moves by a suitable amount or can be prevented from being pulled out downwardly. Further, since the tube 12 cannot be pulled out further, the operator can recognize the end of the operation based on the feeling imparted to the hand thereof. The operator can recognize the end of the operation also from a click feeling when the protrusion 40 is engaged with the engaging hole 76.

As can be clearly seen from FIGS. 8 to 10, when the inner tube 18 is to be slidably moved with respect to the outer tube 20, although the operation lever 44 and the inner tube locking pawl 74 protrude outwardly, since the protruding portions are guarded by the guards 78 in side elevation, even if the operator grips the portions, the fingers of the operator do not hit upon the operation lever 44 and the inner tube locking pawl 74, and the sliding operation is not disturbed.

Figure 11:
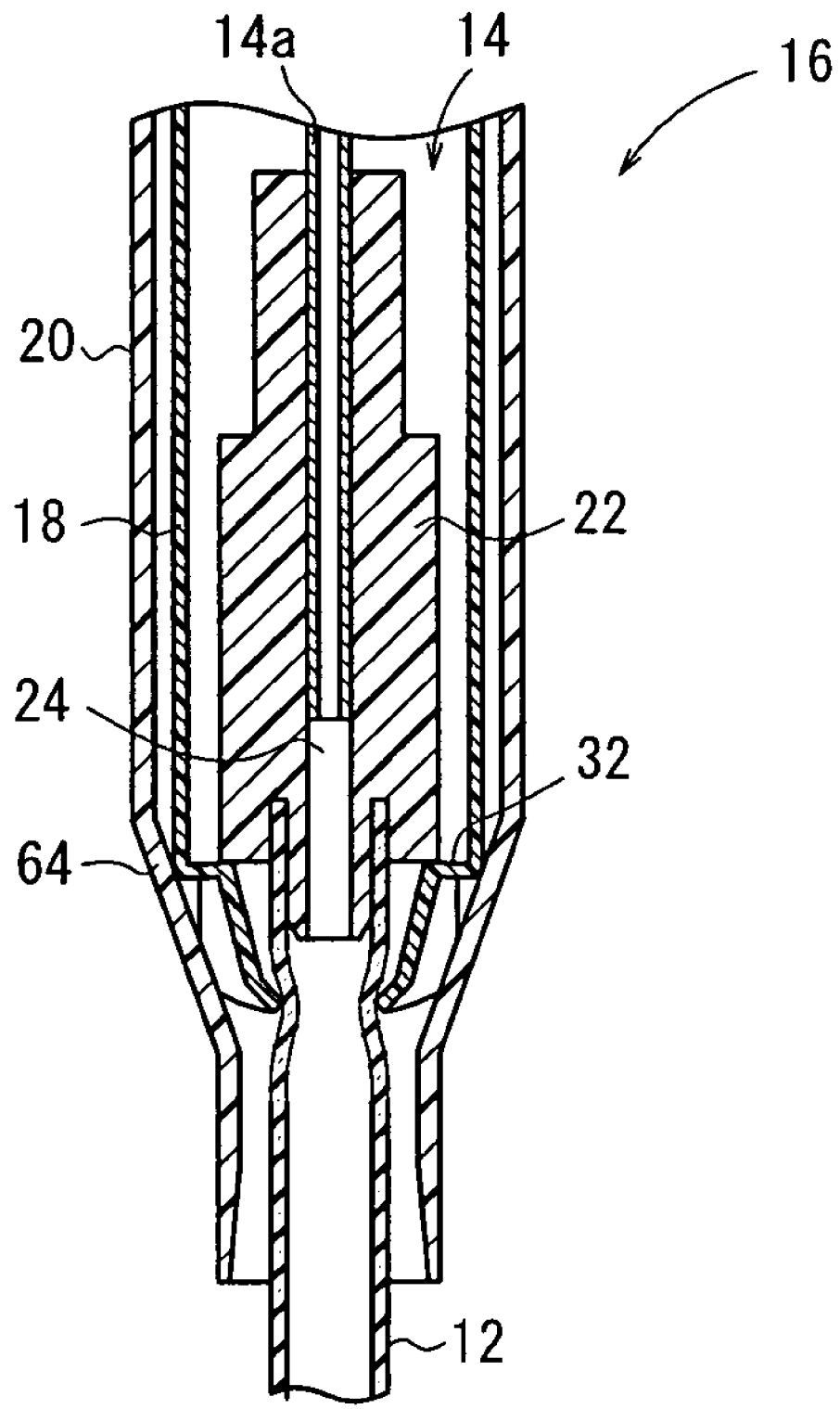
FIG. 11 is an enlarged sectional side elevational view illustrating a manner wherein, when the inner tube slidably moves downwardly, the pawls thereof are brought into close contact with a tube.
Figure 12:
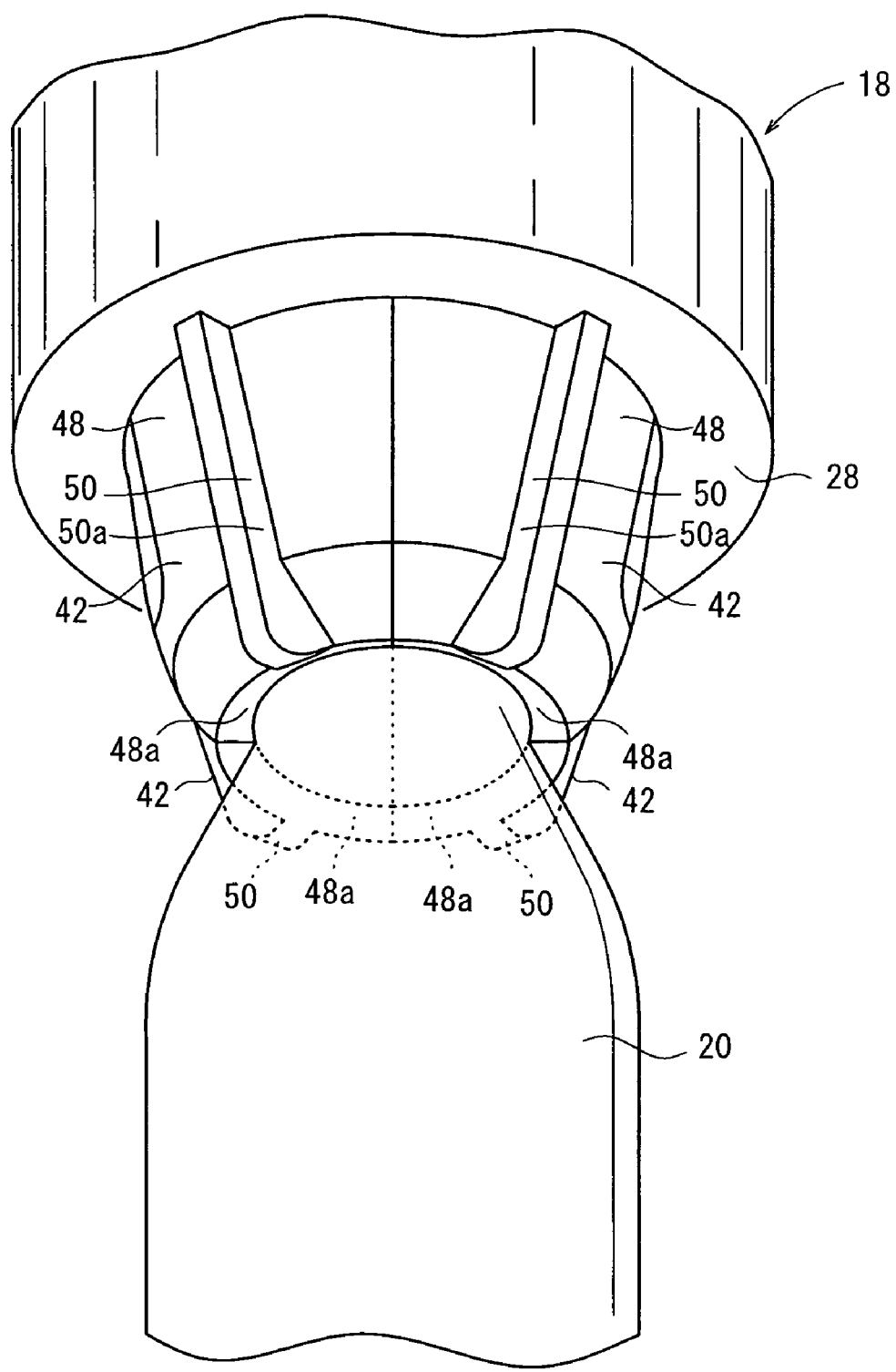
FIG. 12 is a perspective view illustrating a manner wherein, when the inner tube slidably moves downwardly, the pawls thereof are brought into close contact with the tube.

On the other hand, when the tube 12 is pulled out or pushed out from the lower open tube 66 of the protector 16, the four pawls 42 provided at a lower portion of the inner tube 18 is brought into close contact with the tube 12 as shown in FIGS. 11 and 12. In particular, as the inner tube 18 slidably moves downwardly, the outer side surfaces 50a of the guide ribs 50 is brought into contact with and slidably move on the inner surface of the tapering portion 64 to tilt the pawls 42 so as to move toward the center. In other words, the pawls 42 are tilted by an action similar to that of a collet mechanism. Consequently, the respective pawls 42 push the tube 12 from the four sides to contract the tube 12 in a diametrical direction and are brought into close contact with the outer surface of the tube 12.

In this instance, while the tube 12 keeps the cavity thereof in a circular shape, the inner diameter thereof reduces to approximately 0.3 to 1.2 mm, preferably to approximately 0.5 to 1.0 mm. Further, the ends of the pawls 42 are brought into close contact with the outer surface of the tube 12, and the side surfaces of the pawls 42 are brought into close contact with adjacent pawls 42 to place the lower opening 30 of the inner tube 18 into a liquid-tight state.

Further, since the outer side surface 50a is chambered arcuately, smooth sliding movement is possible.

Figure 13:
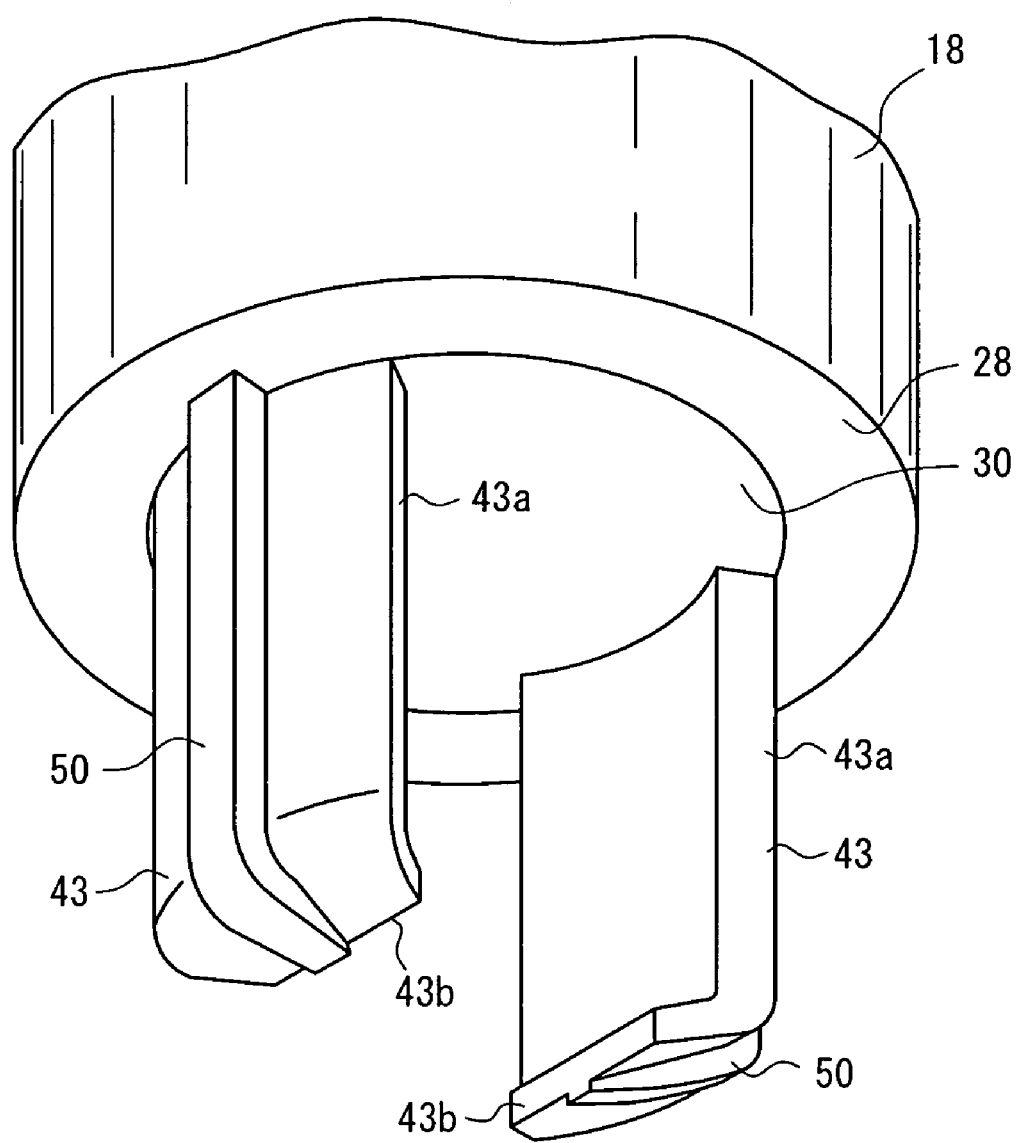
FIG. 13 is a perspective view of a modification to the pawls provided at the lower opening of the inner tube.

The number of the pawls 42 may be a plural number, and, for example, two pawls 43 may be provided as shown in FIG. 13. In this instance, the pawls 43 can sandwich and close up the tube 12. Further, in order to close up the tube 12 certainly, a tip 43b of a plate portion 43a of the pawls 43 may be formed linearly.

Thereafter, the protector 16 is disposed of as a medical waste by a predetermined method together with the blood collection needle 14.

As described above, with the needle set 10 and the protector 16 according to the first embodiment, the inner tube 18 slidably moves with respect to the outer tube 20 to tilt the operation lever 44 to close the lid 38 in an interlocking relationship with movement of the tube 12 and the blood collection needle 14, the blood collection needle 14 accommodated in the inner tube 18 is covered certainly and leakage of blood from the upper opening 34 can be prevented.

Further, in an initial state, the lid 38 is in contact with the back surface plate 68 by a slight resilient action of the hinge 36 and is open stably, and upon use of the blood collection needle 14 for blood collection or the like, the lid 38 does not disturb the movement of the blood collection needle 14 or the tube 12 and allows the hub 22 to move readily after use of the blood collection needle 14.

Furthermore, since the protrusion 40 moves along the guide groove 72 and the operation lever 44 is in engagement with the operation hole 70, the inner tube 18 does not rotate relative to the outer tube 20, and an operation of closing the lid 38 is carried out certainly.

After the lid 38 is closed, the operation lever 44 is engaged with the operation hole 70 to press and bias the lid 38 in a closing direction. Consequently, the lid 38 is closed more certainly to obtain a sealing action. Further, since the inner tube 18 is prevented from reverse movement by the inner tube locking pawl 74 and the engaging hole 76, once the lid 38 is closed, it does not open inadvertently.

Further, the pawls 42 are brought into close contact with the tube 12 in an interlocking relationship with sliding movement of the inner tube 18 and leakage of blood from a lower portion of the tube 12 can be prevented by simple operation.

Now, a protector and a needle set according to second to fourth embodiments are described. In the following description, like portions to those of the needle set 10 and the protector 16 according to the first embodiment are denoted by like reference characters and detailed description thereof is omitted.

Figure 14:
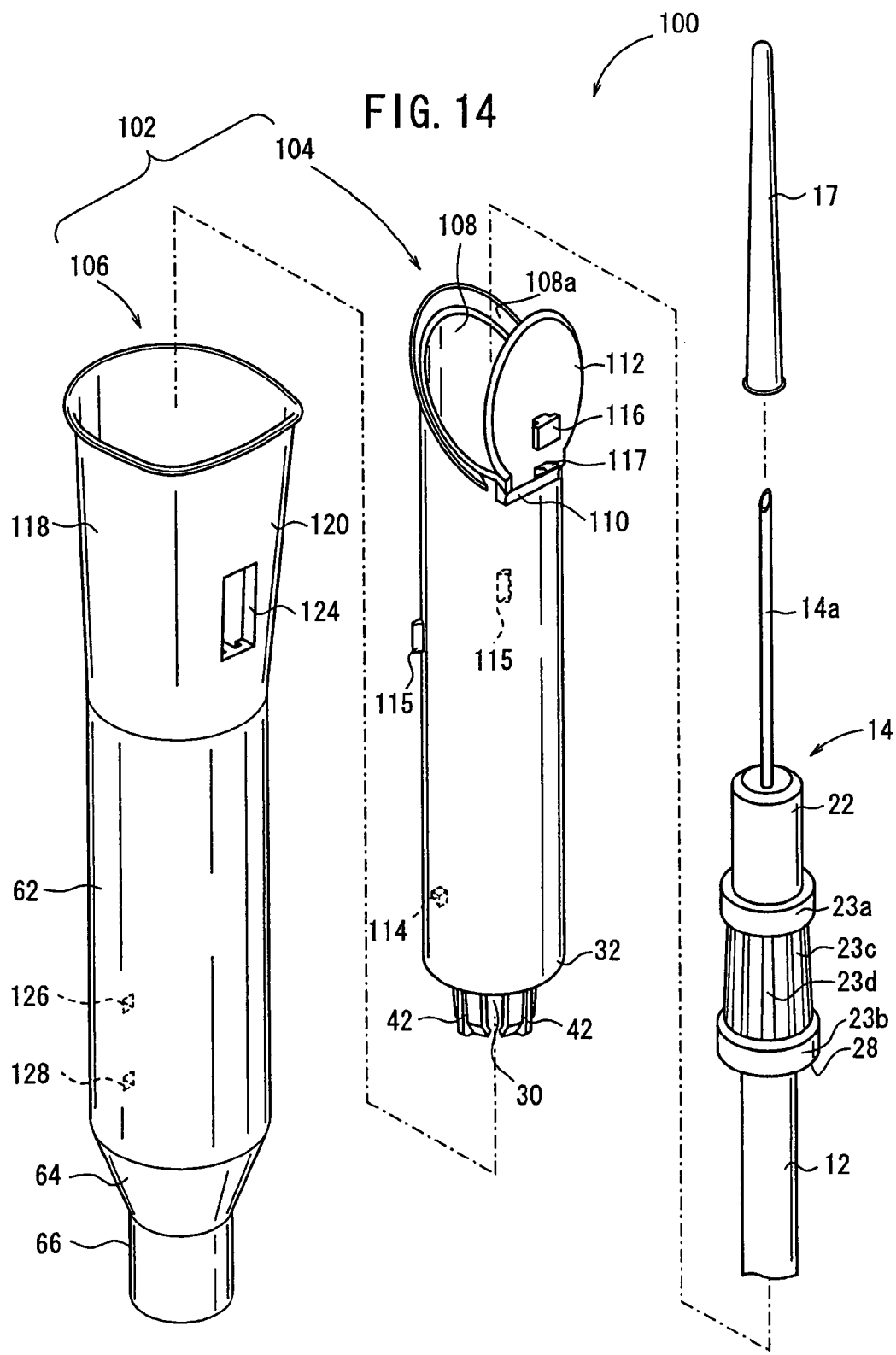
FIG. 14 is an exploded perspective view of a protector according to a second embodiment.

As shown in FIG. 14, a needle set 100 according to the second embodiment is a medical tool similar to the needle set 10 and includes a blood collection needle 14 to which a tube 12 is connected, a protector 102 for protecting the blood collection needle 14 after being used, and a cap 17. The protector 102 includes an inner tube 104, and an outer tube 106 for holding the inner tube 104 for sliding movement in a cavity portion thereof. The inner tube 104 and the outer tube 106 correspond to the inner tube 18 and the outer tube 20, respectively.

The inner tube 104 has a hollow configuration similarly to the inner tube 18, and has a lower opening 30 and pawls 42 near the lower opening 30. The inner tube 104 further has an upper opening 108, a lid 112 connected to the upper opening 108 through a hinge 110, a protrusion 114 provided on a side surface of a lower portion of the inner tube 104, and two guide protrusions 115 provided at a middle height portion of the inner tube 104. The protrusion 114 has a triangular shape in side elevation and has an upper surface in the form of a substantially horizontal upper surface and a lower surface in the form of a moderate inclined surface.

The upper opening 108 is an elliptical opening formed in a slope of approximately 45° as viewed in side elevation, and an outer side portion of an edge portion of the upper opening 108 is formed with a rather great thickness while a shallow annular groove 108a provided on the inner side of the edge portion such that it is fitted with the lid 112 when the lid 112 is closed. The lid 112 is a resin plate of an elliptical shape which can be fitted in the annular groove 108a of the upper opening 108 to close up the upper opening 108, and is connected to a lower end portion of the upper opening 108 through the hinge 110. The lid 112 has, on a side surface thereof, a rail engaging piece 116 provided at a middle portion thereof and an operation lever 117 provided at a lower portion thereof and projecting in an outward direction. The rail engaging piece 116 has a T shape spread to the left and right on the tip side thereof as viewed in top plan view.

The outer tube 106 has an upper open tube 118, a tube body 62, a tapering portion 64 and a lower open tube 66 in the order from above. The upper open tube 118 has a horseshoe shape formed from a combination of a semi-circle and a square as viewed in top plan, and the diameter of the semicircular portion is substantially equal to that of the tube body 62 (refer to FIG. 15). An upper end of the upper open tube 118 is expanded in a trumpet shape and opened. A back surface plate 120 opposing to the semicircular portion is set to an area of a degree such that the lid 112 can rest thereon, and a lower end portion thereof is connected smoothly to the tube body 62.

Figure 15:
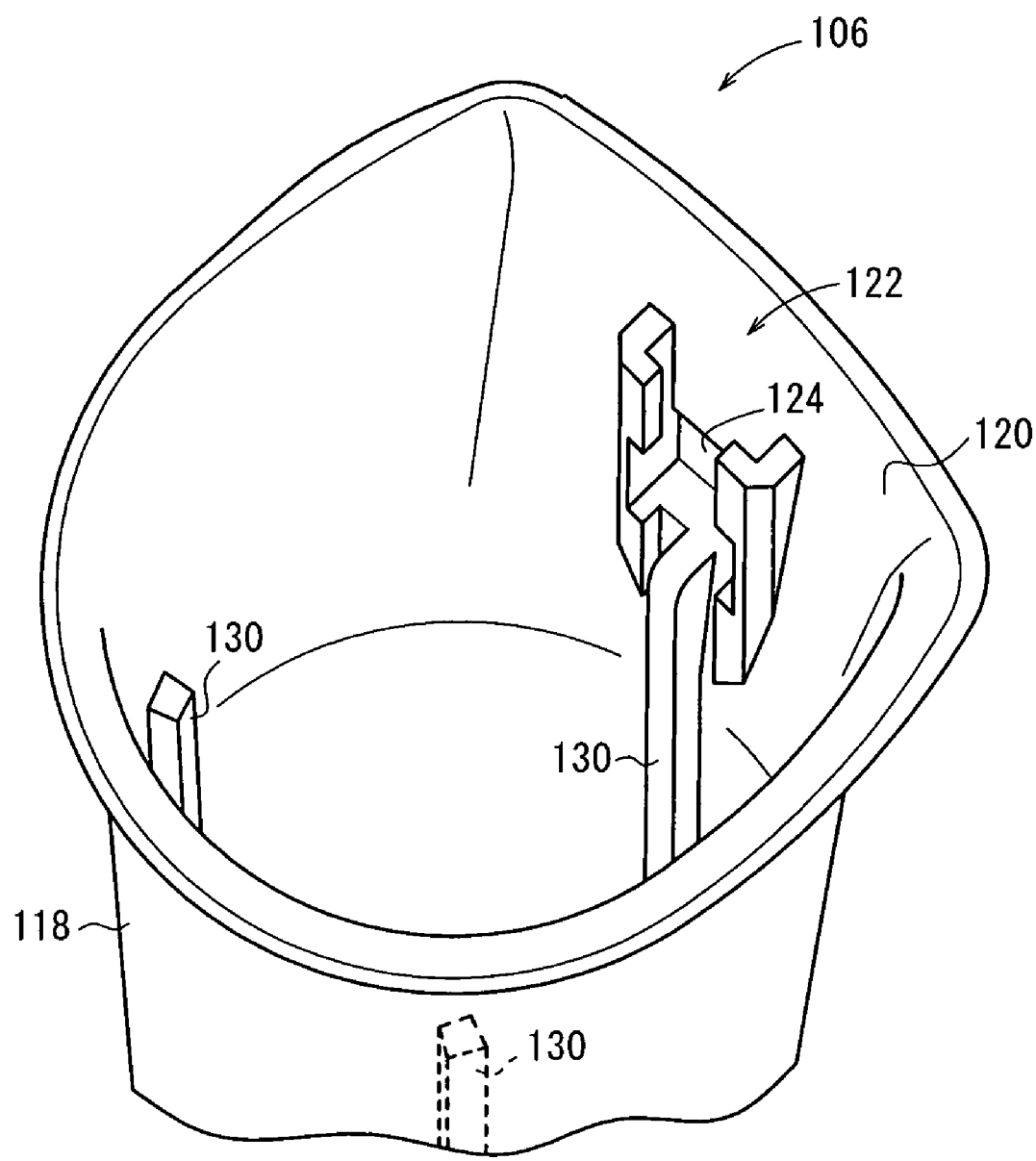
FIG. 15 is an enlarged perspective view of an upper portion of an outer tube according to the second embodiment.

As shown in FIG. 15, a rail 122 and an operation hole (operation means) 124 are provided on the back surface plate 120. The rail 122 is shaped for engagement with the rail engaging piece 116 described hereinabove and provided on the inner side of the back surface plate 120 such that the rail 122 can guide the rail engaging piece 116 in an axial direction. The operation hole 124 is provided in a neighboring relationship below the rail 122 and has a shape rather elongated in the axial direction.

Referring back to FIG. 14, the outer tube 106 further has engaging holes (locking means) 126 and 128, and three adjustment ribs 130 extending in the axial direction on the inner side surface of the tube body 62. The engaging holes 126 and 128 are provided in an aligned relationship with each other in the vertical direction such that the protrusion 114 may be fitted therein when the inner tube 104 is in an initial state and in an operation end state. The adjustment ribs 130 correspond to the adjustment ribs 80 described hereinabove and hold the inner tube 104. Further, one of the adjustment ribs 130 is in contact with a left surface of one of the two guide protrusions 115 while another one of the adjustment ribs 130 is in contact with a right surface of the other guide protrusion 115. In this manner, the guide protrusions 115 act as positioning means for preventing the inner tube 104 from rotating relative to the outer tube 106.

Figure 16:
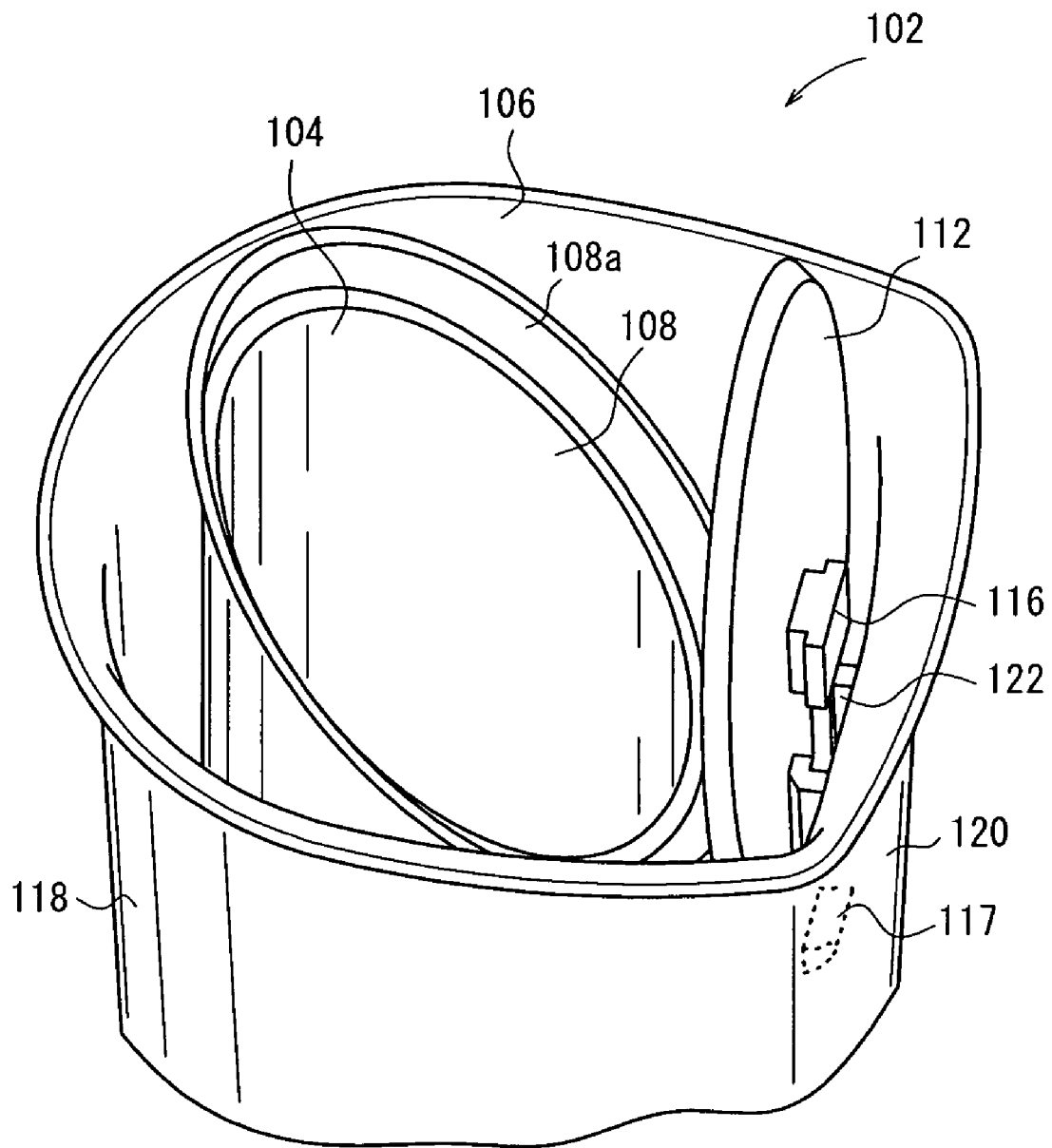
FIG. 16 is an enlarged perspective view of an upper portion of the protector according to the second embodiment upon assembly.

In order to assemble the inner tube 104 to the outer tube 106 to obtain the protector 102, the inner tube 104 is inserted from the upper open tube 118 as shown in FIG. 16. Thereupon, while the operation lever 117 is in contact with and resiliently deformed by the rail 122, the inner tube 104 is inserted while the lid 112 is kept in the vertical orientation.

Figure 17:
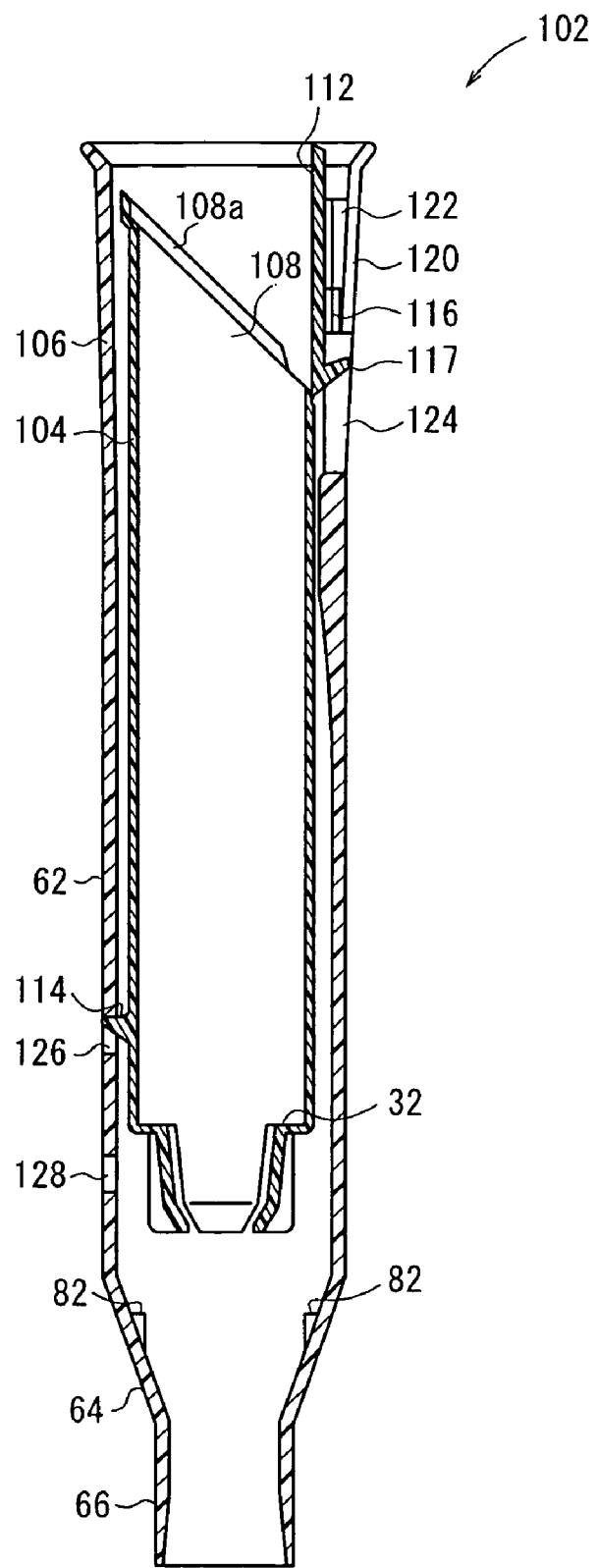
FIG. 17 is a sectional side elevational view of the protector according to the second embodiment.

By further inserting the inner tube 104 into the outer tube 106 as shown in FIG. 17, the rail engaging piece 116 is engaged with the rail 122. When the inner tube 104 is inserted until the rail engaging piece 116 is sufficiently engaged with the rail 122, the operation lever 117 is fitted into an upper portion of the operation hole 124 and the protrusion 114 is fitted into the engaging hole 126. Consequently, the inner tube 104 is placed into an initial state. The operation lever 117 is released from the elastic force exerted from the rail 122 and restores its original shape. Since, in the initial state, the rail engaging piece 116 is held by the rail 122, the opening state of the lid 112 with respect to the upper opening 108 is kept stably independent of the elastic force of the hinge 110 and so forth, and even if the protector 102 is acted upon by vibrations, the lid 112 can be prevented from being shaken or from being closed inadvertently.

In order to store the blood collection needle 14 after being used into the protector 102, the tube 12 and the blood collection needle 14 are moved downwardly similarly as in the needle set 10 described hereinabove. Consequently, after the blood collection needle 14 and the hub 22 are inserted into the inner tube 104 through the upper open tube 118 and the base end portion 28 is engaged with the annular seat surface 32, the inner tube 104 slidably moves downwardly together with the blood collection needle 14 and the hub 22.

Figure 18:
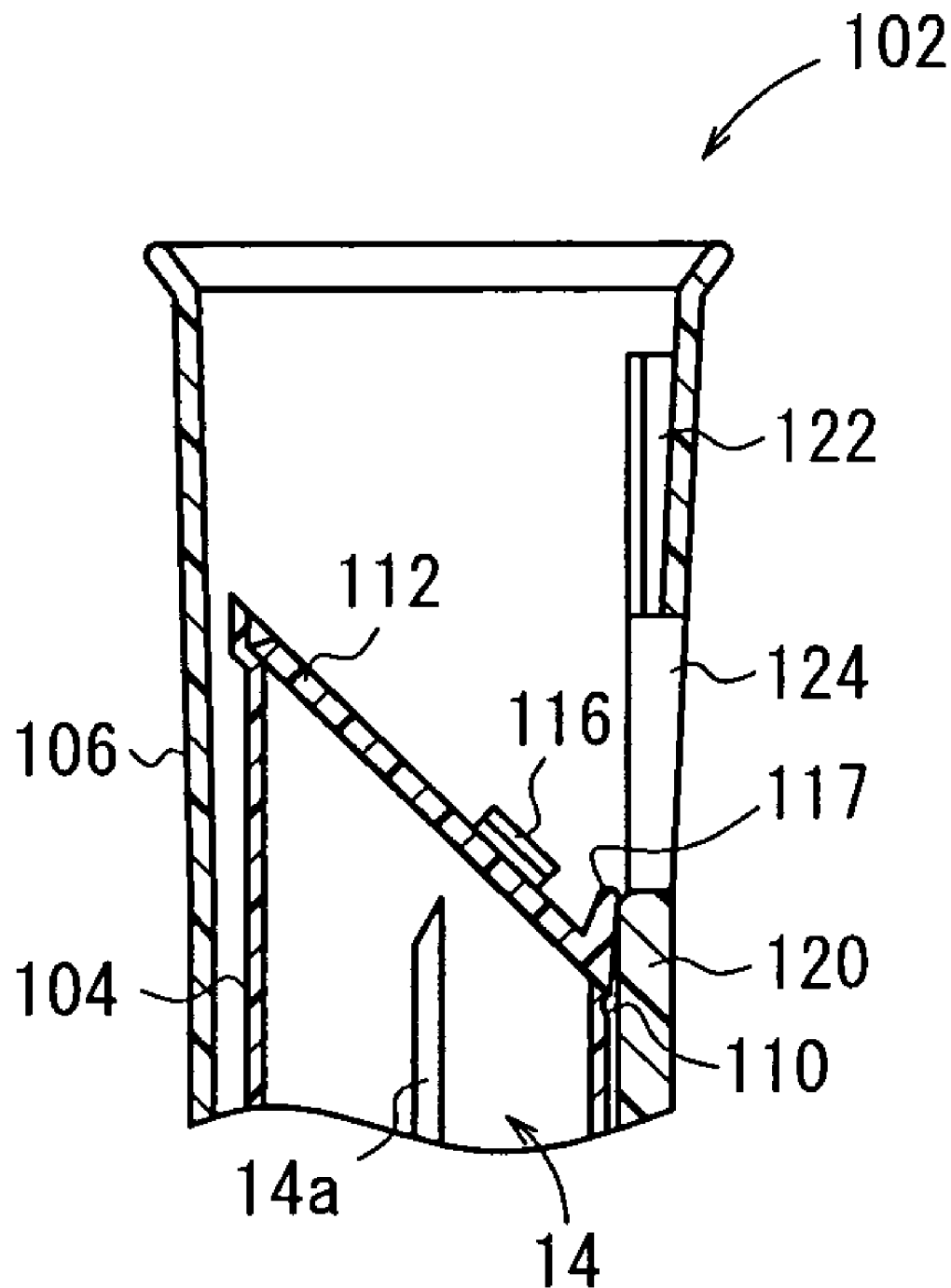
FIG. 18 is a sectional side elevational view showing the protector according to the second embodiment in a state in which the inner tube slidably moves to its operation end position and a lid is closed.

Thereafter, since the rail engaging piece 116 is pulled off and released from below the rail 122, and the operation lever 117 rides on the inner surface of the back surface plate 120 from the operation hole 124 as seen in FIG. 18, the lid 112 is tilted around the hinge 110 to close up the upper opening 108. Further, since the upper opening 108 is set to approximately 45° as viewed in side elevation, the operation lever 117 projecting at approximately 90° with respect to the lid 112 in the initial state is brought into contact with the inner surface of the back surface plate 120 and resiliently deformed to approximately 45° to press and bias the lid 112 suitably in the closing direction. Accordingly, the lid 112 exhibits a sealing action to the upper opening 108 and can seal the inner tube 104.

Further, upon sliding movement of the inner tube 104, the protrusion 114 is released from the engaging hole 126 and slidably moves along the inner surface of the tube body 62, and is fitted into the engaging hole 128 after it moves by a suitable amount. The operator can recognize the end of the operation from a click feeling when the protrusion 114 is fitted into the engaging hole 128. Thereupon, even if an operation such as pushing the tube 12 upwardly should be carried out, since the top surface of the protrusion 114 is a substantially horizontal surface of a triangular shape, reverse movement is prevented, and the lid 112 closed once does not open. Further, the lower opening 30 abuts with the abutment stops 82, and the inner tube 18 is prevented from being pulled off from below.

Figure 19:
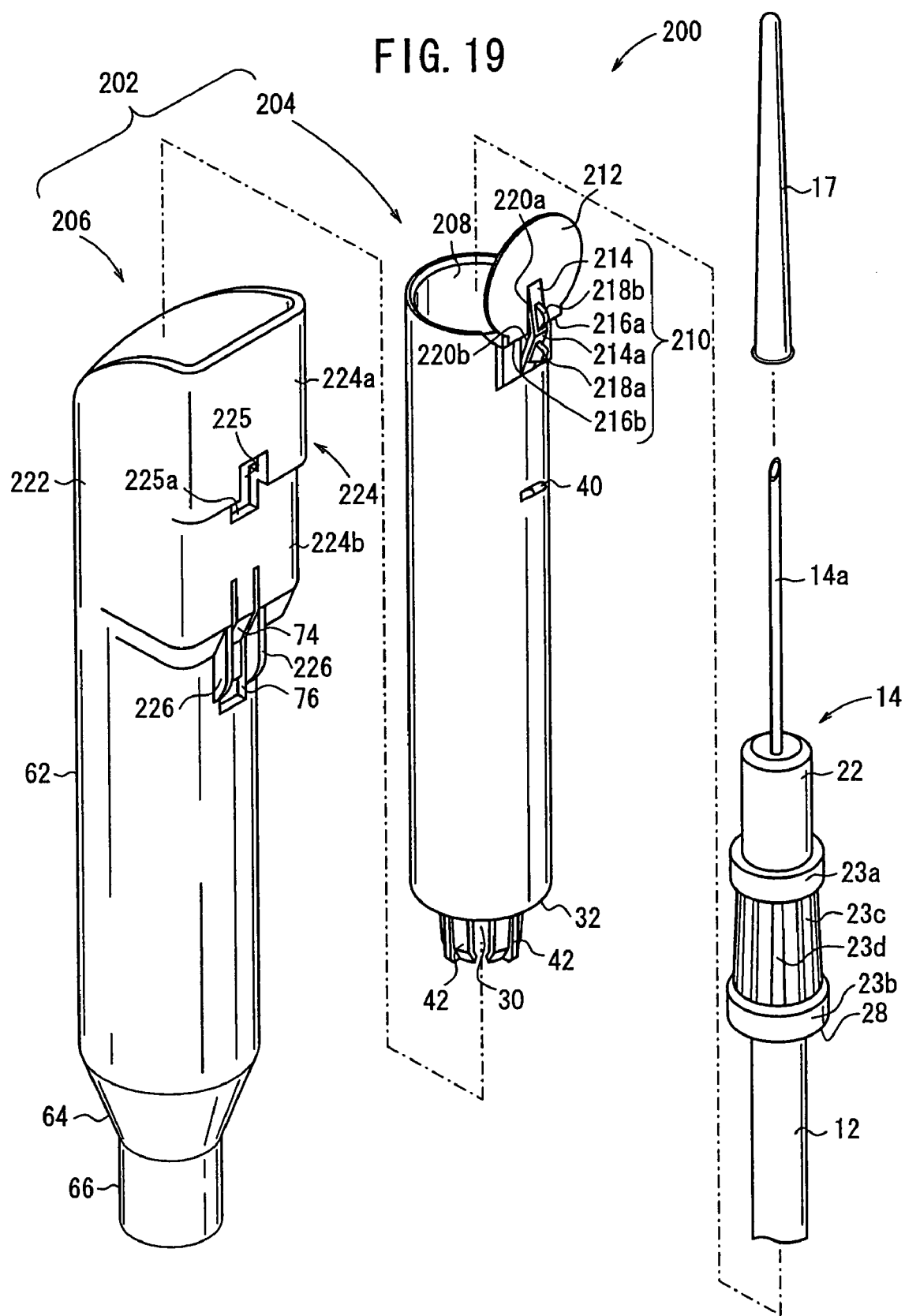
FIG. 19 is an exploded perspective view of a protector according to a third embodiment.

As shown in FIG. 19, the needle set 200 according to the third embodiment is a medical tool similar to the needle set 10 and includes a blood collection needle 14 to which a tube 12 is connected, a protector 202 for protecting the blood collection needle 14 after being used, and a cap 17. The protector 202 includes an inner tube 204, and an outer tube 206 holding the inner tube 204 for sliding movement in a cavity portion thereof. The inner tube 204 and the outer tube 206 correspond to the inner tube 18 and the outer tube 20 described hereinabove, respectively.

The inner tube 204 has a hollow configuration similarly to the inner tube 18 and has pawls 42 at a lower opening 30 thereof. Further, the inner tube 204 has an upper opening 208, and a lid 212 connected to the upper opening 208 through a three-point hinge (also called snap hinge) 210. The upper opening 208 and the lid 212 have shapes substantially similar to those of the upper opening 34 and the lid 38, respectively, but only an attaching portion of the three-point hinge 210 is different. The three-point hinge 210 carries out snap operation of biasing the lid 212 in either an opening direction or a closing direction, and has a biasing hinge 214 bent substantially at a right angle at a bent portion 214a, and pivot hinges 216a and 216b provided on the left and right of the biasing hinge 214.

One upper side end of the biasing hinge 214 is connected to a substantially middle portion of an upper surface of the lid 212, and the other lower side end of the biasing hinge 214 is connected to an outer side surface of the inner tube 204. Lock ribs 218a and 218b each in the form of a small swollen portion are provided at slightly lower and upper side surfaces of the bent portion 214a of the biasing hinge 214. An operation lever (operation means) 218 is formed from the two lock ribs 218a and 218b. At locations of the lid 212 and the inner tube 204 corresponding to the biasing hinge 214, cutouts 220a and 220b are provided. The pivot hinges 216a and 216b hold the lid 212 for pivotal motion with respect to the inner tube 204.

The outer tube 206 has an upper open tube 222, a tube body 62, a tapering portion 64, and a lower open tube 66. The upper open tube 222 has a shape substantially the same as that of the upper open tube 60 described hereinabove, but only a back surface plate 224 is different. The back surface plate 224 has a step at a substantially middle portion thereof, and the upper portion 224a is disposed a little outwardly of the lower portion 224b. The lower portion 224b is set to the same position and same shape as those of the lower portion of the back surface plate 68. An operation hole (operation means) 225 is a hole corresponding to the operation hole 70 described hereinabove.

Two guards 226 correspond to the second swollen portions 78b of the guards 78 and are formed so as to guard inner tube locking pawls 74.

Figure 20:
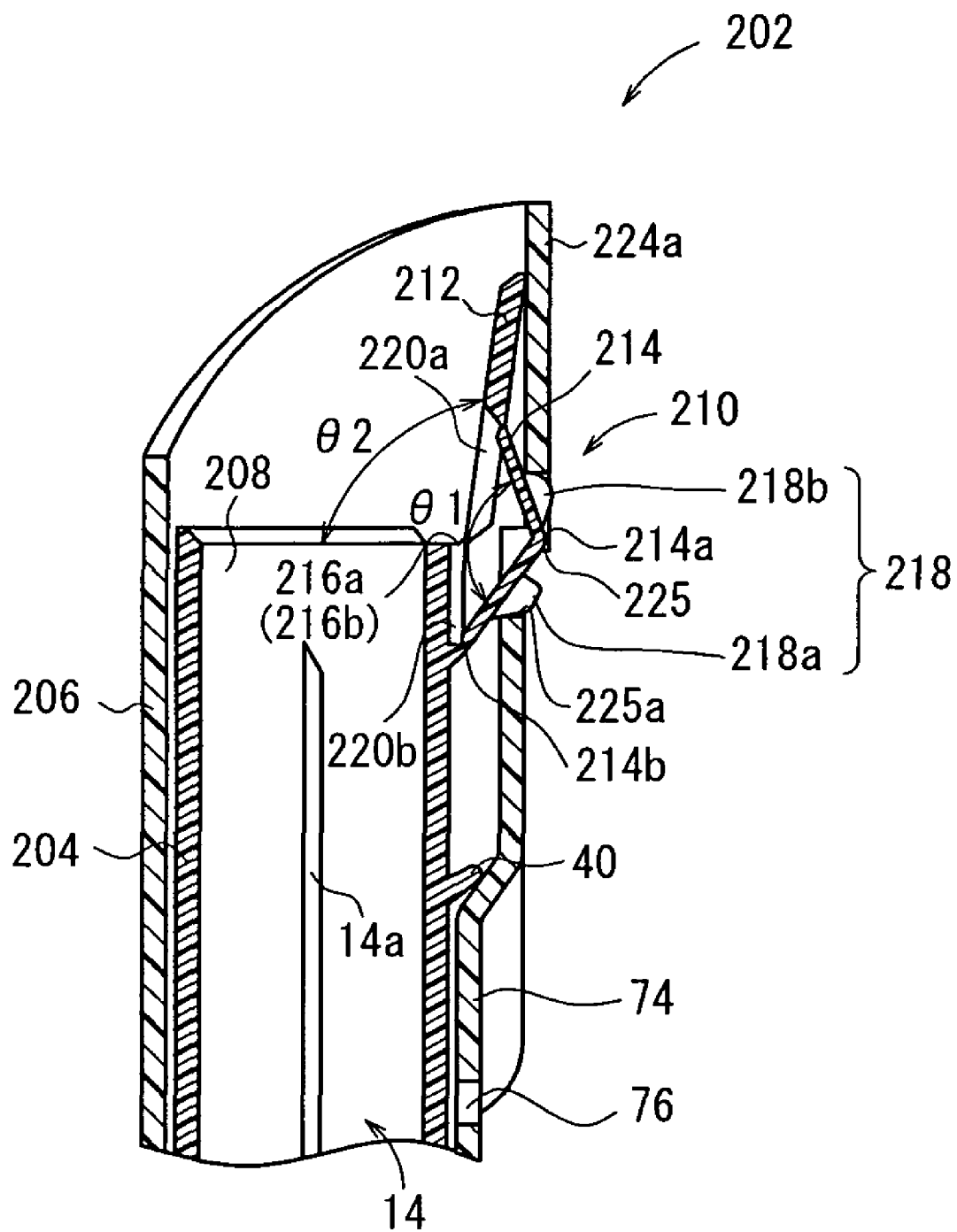
FIG. 20 is a sectional side elevational view of an upper portion of the protector according to the third embodiment.

In order to assemble the inner tube 204 to the outer tube 206 to obtain the protector 202, the inner tube 204 is inserted into the upper open tube 222 from the upper opening 208 side. Thereupon, an end portion of the lid 212 is brought into contact with the inner surface of the upper portion 224a of the back surface plate 224 and the lid 212 is tilted a little in the closing direction as shown in FIG. 20. As the lid 212 is disposed at the position closed a little, also the biasing hinge 214 is tilted a little around the secondary fulcrum 214b, and the bent angle of the bent portion 214a is expanded a little by such tilting motion. Since the bent portion 214a exerts elastic force so as to restore its original angle upon molding, the lid 212 is biased in the opening direction and is pressed against the upper portion 224a. Consequently, the lid 212 is brought into slight contact with the back surface plate 224, and the open state of the lid 212 with respect to the upper opening 208 is kept stably.

Further, since the protrusion 40 engages with the guide groove 72 and the triangular protrusion 72a, the inner tube 204 is held in a correct initial state. When the inner tube 204 is in the initial state, the lock ribs 218a and 218b are fitted with and held stably by an upper end portion and a lower end portion of the operation hole 225. It is to be noted that, as clearly seen from FIG. 20, the lock ribs 218a and 218b and the bent portion 214a scarcely protrude from the operation hole 225. Accordingly, guards corresponding to the first swollen portions 78a described hereinabove are unnecessary.

In order to store the blood collection needle 14 after being used into the protector 202, the tube 12 and the blood collection needle 14 are moved downwardly similarly as in the needle set 10 described hereinabove. Consequently, the blood collection needle 14 and the hub 22 are inserted into the inner tube 204 through the upper open tube 222 of the outer tube 206, and after the base end portion 28 is engaged with the annular seat surface 32, the inner tube 104 slidably moves downwardly together with the blood collection needle 14 and the hub 22.

Figure 21:
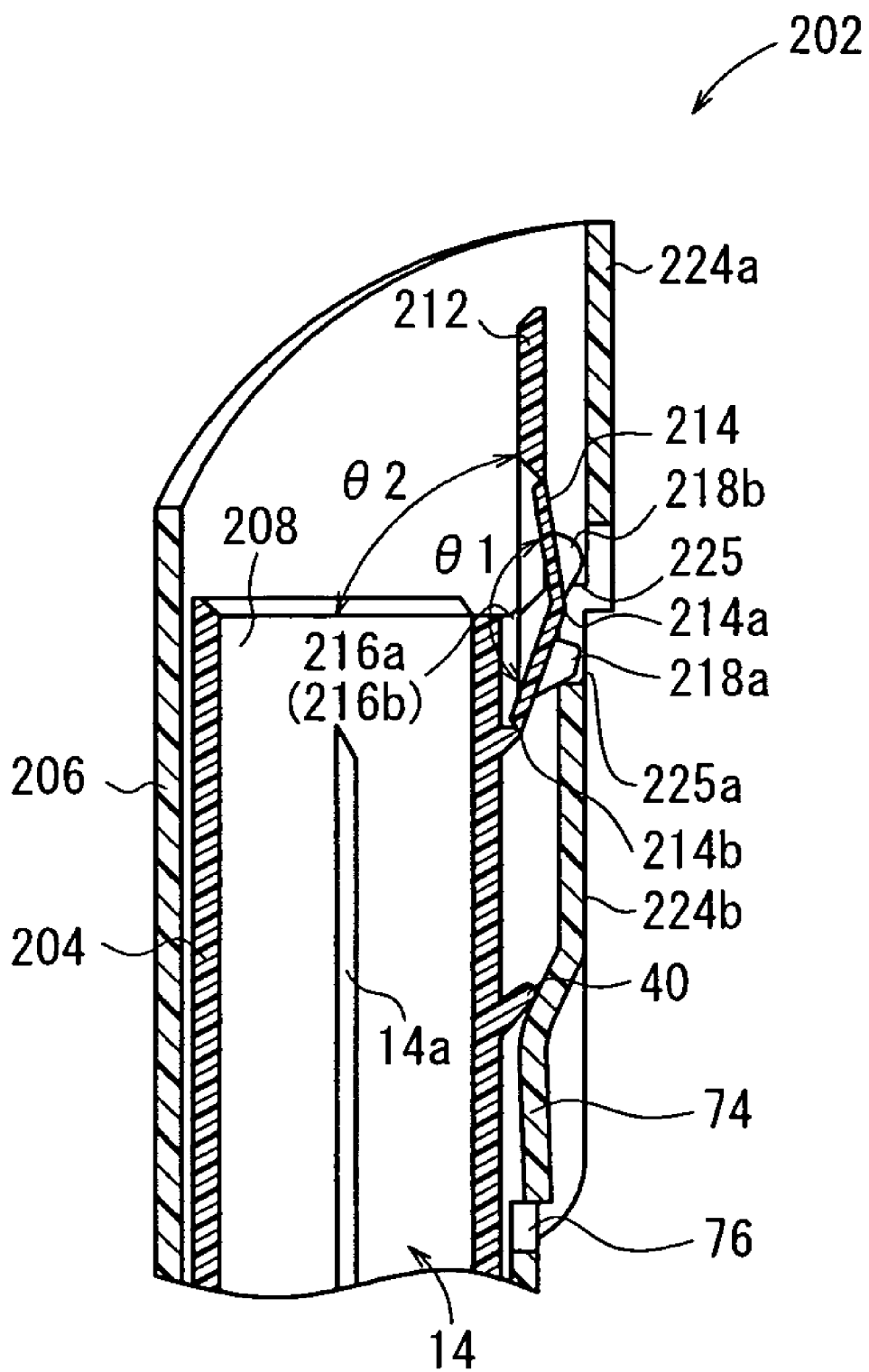
FIG. 21 is a sectional side elevational view showing the protector according to the third embodiment in a state in which an inner tube slidably moves downwardly and a lid is being closed.

Thereafter, since the lock rib 218b on the lower side is brought into contact with and pushed up by the lower end portion 225a of the operation hole 225 as seen in FIG. 21, and the lid 212 is tilted in the closing direction around the pivot hinges 216a and 216b and spaced away from the back surface plate 224. The biasing hinge 214 is tilted around the secondary fulcrum 214b, and the lock rib 218a is pulled out from the operation hole 225.

As the inner tube 204 slidably moves downwardly, the biasing hinge 214 is further tilted around the secondary fulcrum 214b. Thereupon, the bent angle $\theta 1$ of the bent portion 214a is gradually expanded. However, after the angle $\theta 2$ defined by the lid 212 and the upper opening 208 becomes smaller than a predetermined angle (for example, 70°), the bent angle $\theta 1$ of the bent portion 214a is reduced. Since the bent portion 214a exerts elastic force so as to restore the original angle, the lid 212 is thereafter biased in the closing direction and carries out automatically closing snap operation independently of the sliding amount of the inner tube 204. As the lid 212 closes, the biasing hinge 214 is fitted into the cutouts 220a and 220b and the inner tube 204 covers the blood collection needle 14 with little clearance.

Figure 22:
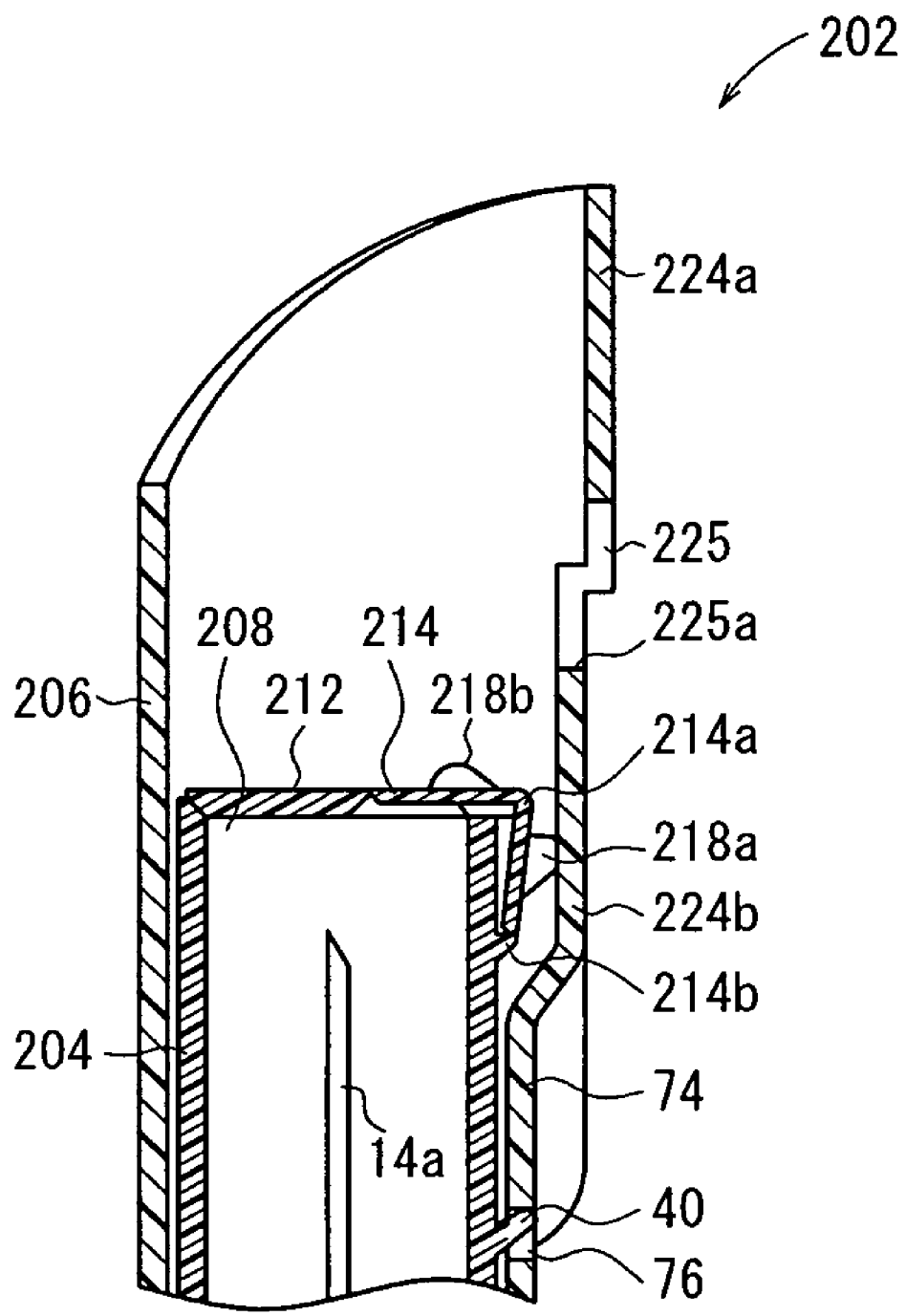
FIG. 22 is a sectional side elevational view showing the protector according to the third embodiment in a state in which the inner tube slidably moves to its operation end position and the lid is closed.

As shown in FIG. 22, when the inner tube 204 slidably moves to the operation end position, the lock rib 218b is brought into contact with and elastically presses the inner surface of the lower portion 224b of the back surface plate 224 so that elastic force to the biasing hinge 214 is further added. Accordingly, after the lid 212 is closed, the operation lever 218 (lock rib 218b) presses and biases the lid 212 in the closing direction. The lid 212 presses the upper opening 208 to close up the upper opening 208 with a higher degree of certainty.

In this manner, with the needle set 200 and the protector 202 according to the third embodiment, the lid 212 can be closed certainly by the three-point hinge 210 of a simple and convenient configuration. Further, when the lid 212 is closed, since suitable snap sound is generated by snapping operation, the operator can aurally confirm the closing operation of the lid 212.

Figure 23:
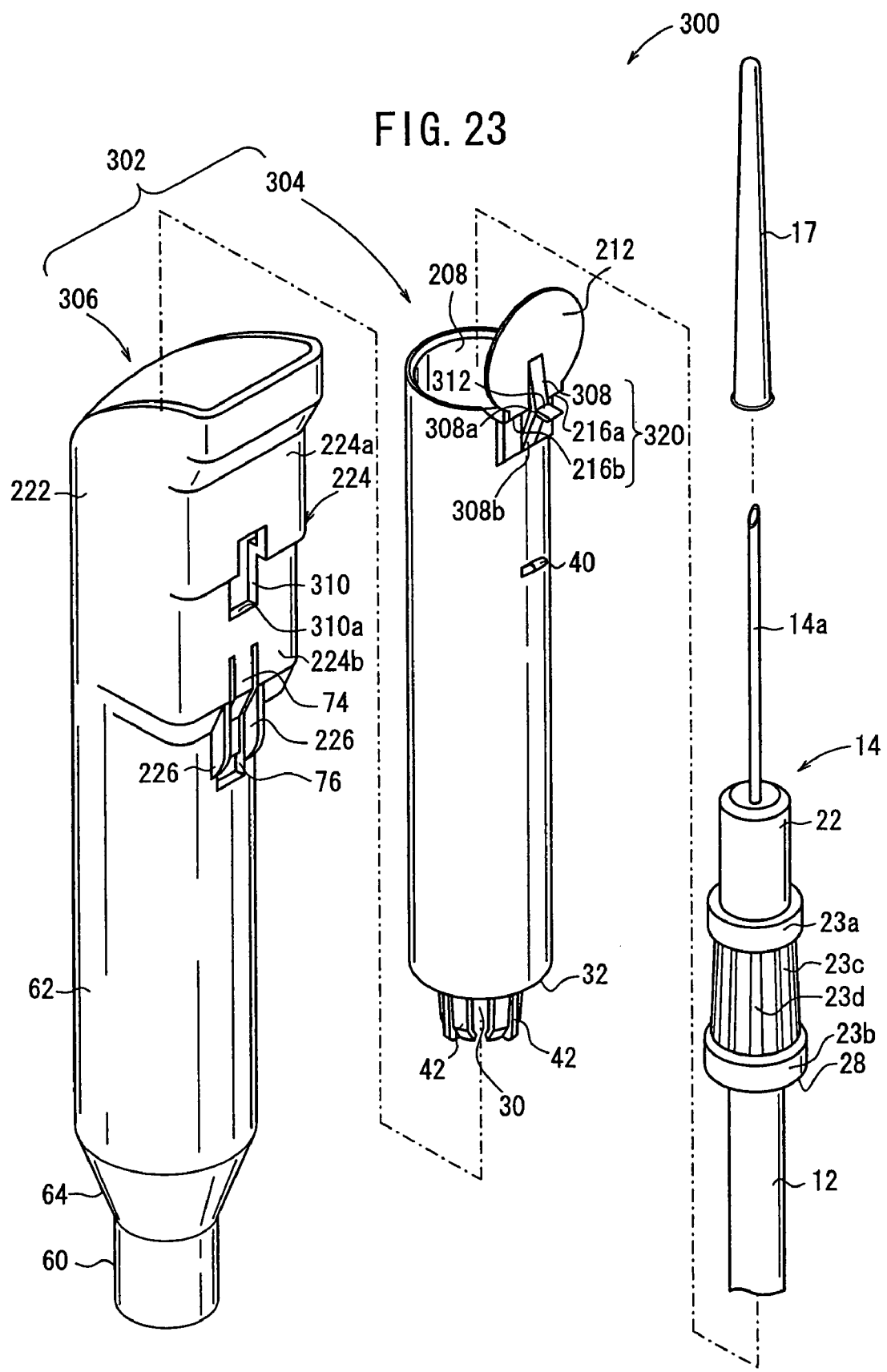
FIG. 23 is an exploded perspective view of a protector according to a fourth embodiment.

Next, as shown in FIG. 23, a needle set 300 and a protector 302 according to the fourth embodiment have structures substantially the same as those of the needle set 200 and the protector 202 described hereinabove, respectively. An inner tube 304, an outer tube 306 and a three-point hinge 320 of the protector 302 correspond to the inner tube 204, outer tube 206 and three-point hinge 210 described hereinabove, respectively, but only a biasing hinge 308 and a operation hole 310 of the three-point hinge 320 are different.

The biasing hinge 308 has a bent shape similar to that of the biasing hinge 214, and one upper side end of the biasing hinge 308 is connected to a substantially middle portion of an upper surface of the lid 212 while the other lower side end is connected to a portion of an outer side surface of the inner tube 304 a little lower than the upper opening 208. Meanwhile, an operation lever (operation means) 312 protrudes from an outer surface of a bent portion 308a. The operation hole 310 is a hole corresponding to the operation hole 225 described hereinabove and is provided in accordance with the position and the size of the operation lever 312.

Figure 24:
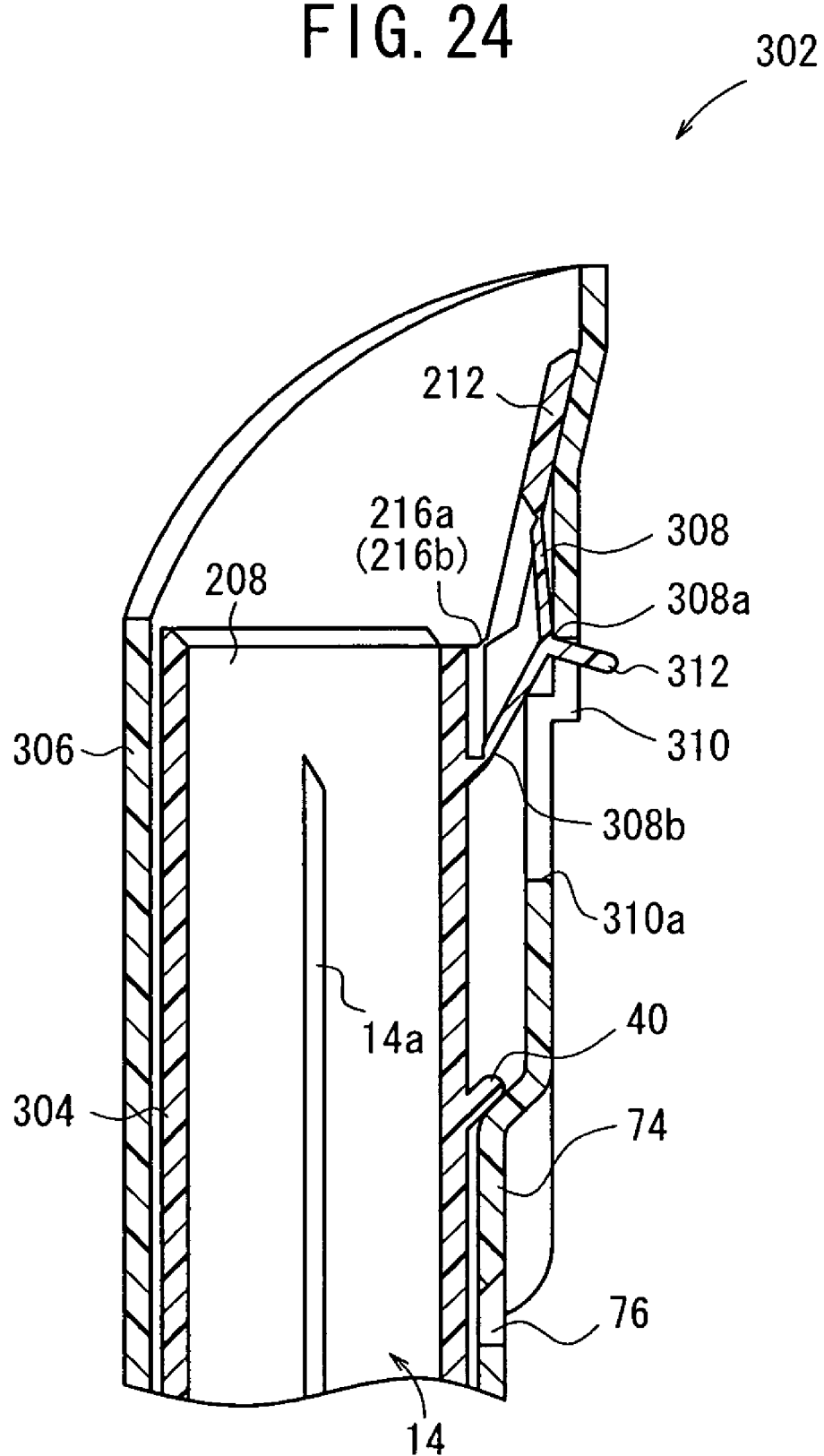
FIG. 24 is a sectional side elevational view of an upper portion of the protector according to the fourth embodiment.

As shown in FIG. 24, when the inner tube 304 is disposed in an initial state, the operation lever 312 fits in an upper end portion of the operation hole 310. At this time, since the bent portion 308a of the biasing hinge 308 exerts elastic force so as to restore the original angle upon molding, the lid 212 is biased in the opening direction and pressed against the upper portion 224a.

Figure 25:
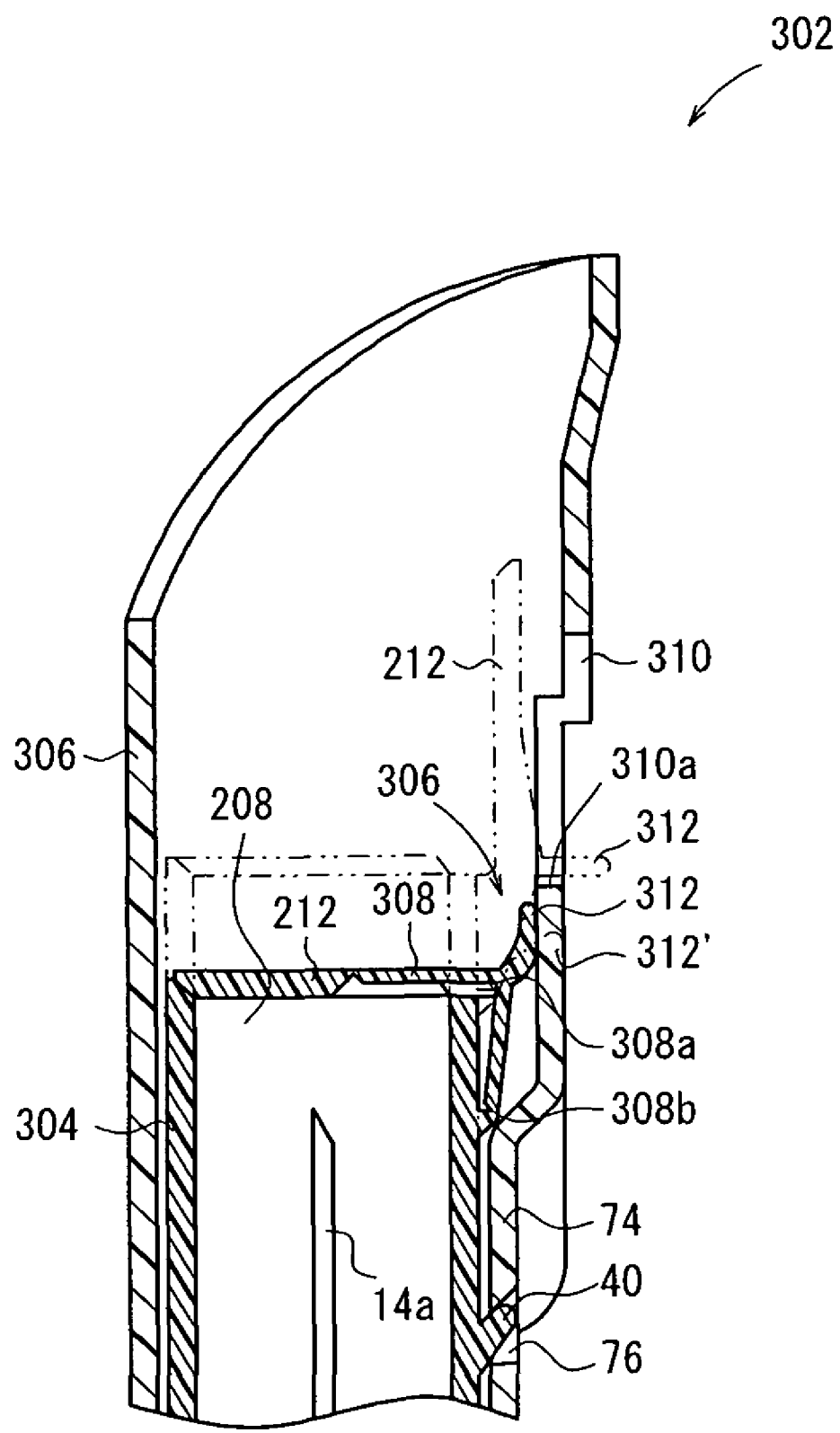
FIG. 25 is a sectional side elevational view showing the protector according to the fourth embodiment in a state in which an inner tube slidably moves to its operation end position and a lid is closed.

As indicated by an alternate long and two short dashes line of FIG. 25, in order to slidably move the inner tube 304 downwardly, the operation lever 312 is brought into contact with and pushed up by a lower end portion 310a of the operation hole 310. Consequently, the lid 212 is tilted in the closing direction around the pivot hinges 216a and 216b and spaced away from the back surface plate 224. At this time, since the operation lever 312 protrudes sufficiently and besides is spaced sufficiently from a secondary fulcrum 308b, the operation lever 312 is brought into contact with the lower end portion 310a certainly and moment of a sufficient magnitude is generated, by which the lid 212 can be tilted more certainly. As the inner tube 304 slidably moves downwardly, the biasing hinge 308 is further tilted around the secondary fulcrum 308b to automatically close the lid 212 similarly to the biasing hinge 214 described hereinabove.

As shown in FIG. 25, when the inner tube 304 slidably moves to the operation end position, the operation lever 312 is brought into contact with the inner surface of the lower portion 224b of the back surface plate 224, and is resiliently bent when compared with the original shape represented by an alternate long and two short dashes line 312'. Consequently, the elastic force to the biasing hinge 308 is further added. Accordingly, the lid 212 can press the upper opening 208 to seal the upper opening 208 more certainly.

In particular, after the lid 212 is closed, the operation lever 312 presses and biases the lid 212 in the closing direction.

Figure 26A:
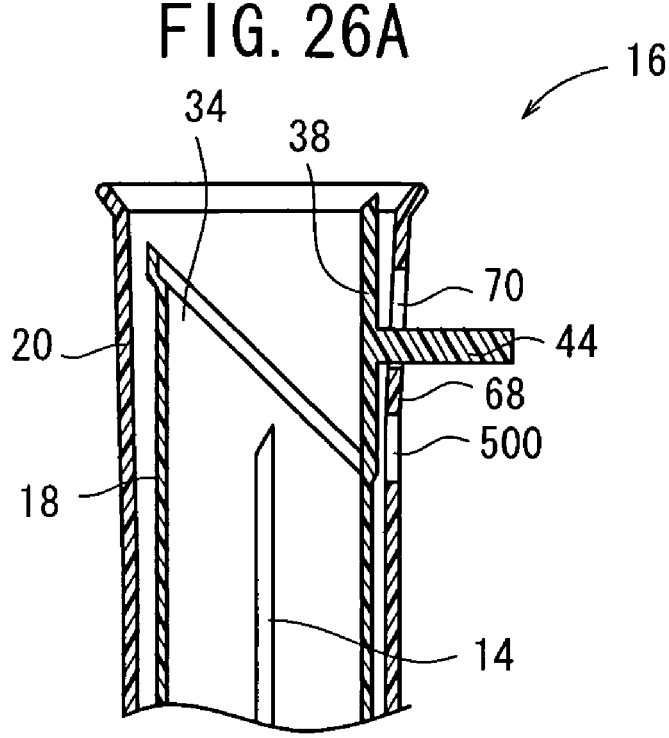
FIG. 26A is a sectional side elevational view of the protector wherein an operation lever extends in a substantially right-angled direction from a portion in the proximity of the middle of an outer surface portion of the lid.
Figure 26B:
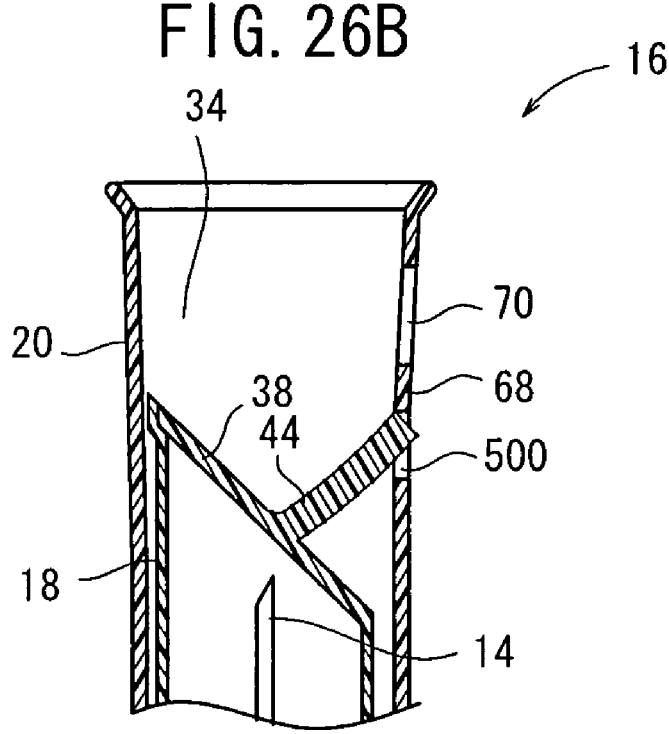
FIG. 26B is a sectional side elevational view illustrating a state wherein the lid of the protector shown in FIG. 26A is closed.

Further, as a modification to the protector 16 described hereinabove, the operation lever 44 may be provided such that, as shown in FIG. 26A, the operation lever 44 extends in a direction substantially right-angularly with respect to the lid 38 from a portion of an outer surface of the lid 38 in the proximity of the center of the same and protrudes from the operation hole 70. In this instance, as the inner tube 18 slidably moves with respect to the outer tube 20, the operation lever 44 is tilted while being removed from the operation hole 70 and acts to close the lid 38. Thereafter, as shown in FIG. 26B, the operation lever 44 can be released from the operation hole 70, ride on the back surface plate 68 of the outer tube 20 and engage with a lower engaging hole 500 to bias the lid 38. Consequently, the lid 38 can be prevented from opening inadvertently and the inner tube 18 can be prevented from moving reversely.

While, in the embodiments described above, an example in which the operation lever 44, 117 or 312 or lock rib 218a provided on the lid 38, 112, 212 is tilted by the engagement with a predetermined location of the outer tube 20, 106, 206 and, as a result, the lid 38, 112, 212 is closed, the operation lever for closing the lid provided on the inner tube may be provided on the outer tube.

As shown in FIG. 27A, for example, a bow-shaped operation lever 400 may be provided on an inner surface of the back surface plate 68 of the outer tube 20 such that, in an initial state, the operation lever 400 is in contact with a side surface of the inner tube 18 so as to be resiliently deformed upwardly.

In this instance, if the inner tube 18 slidably moves down as seen in FIG. 27B, then the operation lever 400 substantially can restore its shape upon molding and directed obliquely downwardly to press the upper surface of the lid 38 to close the lid 38. At this time, the operation lever 400 does not fully restore its shape upon molding but some elastic deformation remains such that the lid 38 can be pressed suitably.

The protectors 16, 102, 202, 302 and the needle set 10, 100, 200, 300 according to the present embodiments are not limited to those for the blood collection needle 14 but naturally can be applied suitably to other medical needles for blood transfusion, infusion and so forth.

The invention claimed is:

1. A protector into which a tube having a needle provided at one end thereof and a blood bag provided at another end thereof is inserted and which accommodates and protects said needle after being used, comprising:
   an inner tube including a stopper which is brought into contact with said needle when said needle is accommodated in said inner tube from one opening thereof, and a lid connected to said one opening through a hinge;
   an outer tube configured to hold said inner tube for sliding movement in a cavity portion thereof;
   an operation lever provided on an outer surface of said lid; and
   operation means configured to operate said operation lever to contact said outer tube, when said needle, after being used, is brought into contact with said stopper to slidably move said inner tube with respect to said outer tube, so as to close said lid, wherein
   said inner tube has a plurality of pawls provided at an end portion of another opening;
   said outer tube has a tapering portion provided on an inner surface thereof; and
   said plurality of pawls are brought into contact with said tapering portion and displaced inward, when said needle, after being used, is brought into contact with said stopper to slidably move said inner tube with respect to said outer tube, so as to contract said tube having the needle in a diametrical direction and closely contact said plurality of pawls with said tube having the needle.

2. The protector according to claim 1, further comprising:
   holding means configured to hold said lid in an open state before said lid is closed.

3. The protector according to claim 1, further comprising:
   locking means configured to prevent reverse movement of said inner tube, when said inner tube slidably moves by a predetermined amount with respect to said outer tube.

4. The protector according to claim 1, further comprising:
   positioning means configured to prevent said inner tube from rotating with respect to said outer tube.

5. The protector according to claim 1, wherein said operation lever is configured to bias said lid in a closing direction after said lid is closed.

6. A needle set, comprising:
   a protector according to claim 1; and
   a needle to which said tube having the needle is connected.

7. The protector according to claim 1, wherein said operation means comprises an operation hole formed on said outer tube.

8. The protector according to claim 1, wherein said plurality of pawls comprises two pawls, and said two pawls are brought into contact with said tapering portion and displaced to the inner side, when said inner tube slidably moves with respect to said outer tube, so as to sandwich and close up said tube having the needle.

9. A protector into which a tube having a needle provided at one end thereof and a blood bag provided at another end thereof is inserted and which accommodates and protects said needle after being used, comprising:
- an inner tube including a stopper configured to be brought into contact with said needle when said needle is accommodated in said inner tube from one opening thereof, and a lid connected to said one opening through a hinge; and
- an outer tube configured to hold said inner tube for sliding movement in a cavity thereof;
- said inner tube having two pawls provided at an end portion of another opening;
- said outer tube having a tapering portion provided on an inner surface thereof;
- said two pawls being brought into contact with said tapering portion and displaced to the inner side, when said needle, after being used, is in contact with said stopper to slidably move said inner tube with respect to said outer tube, so as to sandwich and close up said tube having the needle.

10. A needle set, comprising:
a protector according to claim 9; and
a needle to which said tube having the needle is connected.

11. The protector according to claim 9, further comprising:
- an operation lever provided on an outer surface of said lid or an inner surface of said outer tube; and
- operation means configured to operate said operation lever to contact said outer tube or said lid, when said inner tube is slidably moved with respect to said outer tube, so as to close said lid.

* * * * *

UNITED STATES PATENT AND TRADEMARK OFFICE
CERTIFICATE OF CORRECTION

| | | |
|---|---|---|
| PATENT NO. | : 8,096,977 B2 | Page 1 of 1 |
| APPLICATION NO. | : 12/084152 | |
| DATED | : January 17, 2012 | |
| INVENTOR(S) | : Masahiro Akiyama et al. | |

It is certified that error appears in the above-identified patent and that said Letters Patent is hereby corrected as shown below:

Title page, Item (75) Inventors, delete "Masahiro Ayiyama" and replace with -- Masahiro Akiyama --.

Signed and Sealed this
Third Day of April, 2012

David J. Kappos
*Director of the United States Patent and Trademark Office*

UNITED STATES PATENT AND TRADEMARK OFFICE
CERTIFICATE OF CORRECTION

PATENT NO.         : 8,096,977 B2
APPLICATION NO.    : 12/084152
DATED              : January 17, 2012
INVENTOR(S)        : Masahiro Akiyama et al.

It is certified that error appears in the above-identified patent and that said Letters Patent is hereby corrected as shown below:

Title page, Item (56) Reference Cited, Foreign Patent Documents, delete "JP 2 237 201 A 5/1991" and replace with --GB 2 237 201 A 5/1991--.

Second page, Foreign Patent Documents continued, delete "JP 2 345 854 A 7/2000" and replace with --GB 2 345 854 A 7/2000--.

Signed and Sealed this
Eighth Day of May, 2012

David J. Kappos
*Director of the United States Patent and Trademark Office*